United States Patent
Nair et al.

(10) Patent No.: US 12,365,872 B2
(45) Date of Patent: Jul. 22, 2025

(54) METHODS FOR DIFFERENTIATING PLURIPOTENT STEM CELLS IN DYNAMIC SUSPENSION CULTURE

(71) Applicant: Lineage Cell Therapeutics, Inc., Carlsbad, CA (US)

(72) Inventors: Rekha R. Nair, Mountain View, CA (US); Stephanie Kayser, Mountain View, CA (US); Abhirath S. Parikh, Los Angeles, CA (US); Uzma Shoukat-Mumtaz, Fremont, CA (US); Erik Michael Whiteley, Concord, CA (US); Nathan C. Manley, San Jose, CA (US); Craig R. Halberstadt, Pleasanton, CA (US)

(73) Assignee: LINEAGE CELL THERAPEUTICS, INC., Carlsbad, CA (US)

( * ) Notice: Subject to any disclaimer, the term of this patent is extended or adjusted under 35 U.S.C. 154(b) by 923 days.

(21) Appl. No.: 17/277,548

(22) PCT Filed: Sep. 19, 2019

(86) PCT No.: PCT/US2019/052015
§ 371 (c)(1),
(2) Date: Mar. 18, 2021

(87) PCT Pub. No.: WO2020/061371
PCT Pub. Date: Feb. 6, 2020

(65) Prior Publication Data
US 2022/0267723 A1      Aug. 25, 2022

Related U.S. Application Data

(60) Provisional application No. 62/733,621, filed on Sep. 19, 2018.

(51) Int. Cl.
*C12N 5/00* (2006.01)
*C12N 5/079* (2010.01)

(52) U.S. Cl.
CPC ......... *C12N 5/0622* (2013.01); *C12N 5/0068* (2013.01); *C12N 2500/46* (2013.01);
(Continued)

(58) Field of Classification Search
CPC ........................... C12N 5/0622; C12N 5/0068
See application file for complete search history.

(56) References Cited

U.S. PATENT DOCUMENTS

| 6,280,718 B1 | 8/2001 | Kaufman et al. |
| 7,285,415 B2 | 10/2007 | Keirstead et al. |

(Continued)

FOREIGN PATENT DOCUMENTS

| CN | 1833021 A | 9/2006 |
| CN | 1852971 A | 10/2006 |

(Continued)

OTHER PUBLICATIONS

Li et al. Targeting the TGF-β signaling pathway for fibrosis therapy: a patent review (2015-2020). Expert Opinion of Therapeutic Patents 31: 723-743. (Year: 2021).*

(Continued)

*Primary Examiner* — Arthur S Leonard
*Assistant Examiner* — Keenan A Bates
(74) *Attorney, Agent, or Firm* — Mintz, Levin, Cohn, Ferris, Glovsky and Popeo, P.C.

(57) ABSTRACT

Methods for differentiating pluripotent stem cells to neuroectoderm in dynamic suspension culture using small molecule or protein inhibitors of TGFβ/Activin/Nodal signaling and BMP signaling are provided. Also provided are methot and protocols for differentiating pluripotent stem cells such as human embryonic stem cells first to neuroectoderm, then (Continued)

further to glial progenitor cells, and further to oligodendrocyte progenitor cells (OPCs), and compositions obtained thereby. The methods of the present disclosure reproducibly produce neuroectoderm progenitor cells by day 7 of the differentiation process, glial progenitor cells by day 21 of the differentiation process and OPCs by day 42 of the differentiation process.

15 Claims, 7 Drawing Sheets

(52) U.S. Cl.
CPC .... *C12N 2501/11* (2013.01); *C12N 2501/115* (2013.01); *C12N 2501/135* (2013.01); *C12N 2501/15* (2013.01); *C12N 2501/155* (2013.01); *C12N 2501/16* (2013.01); *C12N 2501/385* (2013.01); *C12N 2501/41* (2013.01); *C12N 2506/02* (2013.01); *C12N 2506/03* (2013.01); *C12N 2506/45* (2013.01); *C12N 2533/52* (2013.01)

(56) References Cited

U.S. PATENT DOCUMENTS

| | | |
|---|---|---|
| 7,390,659 B2 | 6/2008 | Jessell et al. |
| 7,524,489 B2 | 4/2009 | Messina et al. |
| 7,579,188 B2 | 8/2009 | Keirstead et al. |
| 8,137,969 B2 | 3/2012 | Reubinoff et al. |
| 8,227,247 B2 | 7/2012 | Zhang et al. |
| 8,911,777 B2 | 12/2014 | Coulter |
| 9,238,794 B2 | 1/2016 | Shogbon et al. |
| 9,862,925 B2 | 1/2018 | Aharonowiz et al. |
| 9,969,974 B2 * | 5/2018 | Tesar .................... A61K 35/30 |
| 10,138,292 B2 | 11/2018 | Tryggvason et al. |
| 10,286,009 B2 | 5/2019 | Wirth, III et al. |
| 10,301,592 B2 | 5/2019 | Fossati et al. |
| 10,450,546 B2 | 10/2019 | Goldman et al. |
| 10,676,716 B2 | 6/2020 | Fossati et al. |
| 2004/0009593 A1 | 1/2004 | Keirstead et al. |
| 2010/0015702 A1 | 1/2010 | Rao et al. |
| 2010/0158878 A1 | 6/2010 | Capela et al. |
| 2010/0159595 A1 | 6/2010 | Zhang et al. |
| 2010/0166720 A1 | 7/2010 | Vanderhaeghen et al. |
| 2010/0239541 A1 | 9/2010 | Johe et al. |
| 2011/0059055 A1 | 3/2011 | Goldman et al. |
| 2012/0100113 A1 | 4/2012 | Tesar et al. |
| 2012/0177614 A1 | 7/2012 | Kido |
| 2013/0004467 A1 | 1/2013 | Goldman et al. |
| 2013/0143805 A1 | 6/2013 | Whittaker et al. |
| 2013/0210109 A1 | 8/2013 | Lebkowski et al. |
| 2013/0280219 A1 | 10/2013 | Shiels |
| 2014/0170634 A1 | 6/2014 | Woods |
| 2014/0186955 A1 | 7/2014 | Vanderhaeghen et al. |
| 2014/0248696 A1 | 9/2014 | Zhang et al. |
| 2015/0017139 A1 | 1/2015 | Huang et al. |
| 2015/0050667 A1 | 2/2015 | Carson et al. |
| 2015/0224331 A1 | 8/2015 | Marsala |
| 2016/0015707 A1 | 1/2016 | Tesar et al. |
| 2016/0030490 A1 | 2/2016 | Lanza et al. |
| 2016/0075994 A1 | 3/2016 | Tesar et al. |
| 2016/0152950 A1 | 6/2016 | Zhang et al. |
| 2016/0331786 A1 | 11/2016 | Wirth et al. |
| 2018/0237748 A9 | 8/2018 | Chambers et al. |
| 2019/0262405 A1 | 8/2019 | Wirth et al. |
| 2019/0336538 A1 | 11/2019 | Wirth et al. |
| 2020/0231932 A1 | 7/2020 | Onishi et al. |
| 2021/0189335 A1 | 6/2021 | Whiteley et al. |
| 2023/0139899 A1 | 5/2023 | Onishi et al. |

FOREIGN PATENT DOCUMENTS

| | | |
|---|---|---|
| CN | 102160546 A | 8/2011 |
| CN | 102803472 A | 11/2012 |
| CN | 105624116 A | 6/2016 |
| CN | 107109367 A | 8/2017 |
| JP | 2003533224 A | 11/2003 |
| JP | 2006517084 A | 7/2006 |
| JP | 2010536357 A | 12/2010 |
| JP | 2011514147 A | 5/2011 |
| JP | 2017511153 A | 4/2017 |
| JP | 2022501049 A | 1/2022 |
| KR | 20090035372 A | 4/2009 |
| WO | 9848001 A1 | 10/1998 |
| WO | 0128342 A1 | 4/2001 |
| WO | 0188104 A2 | 11/2001 |
| WO | 2004007665 A2 | 1/2004 |
| WO | 2005007797 A2 | 1/2005 |
| WO | 2009097421 A1 | 8/2009 |
| WO | 2010151782 A1 | 12/2010 |
| WO | 2012096705 A1 | 7/2012 |
| WO | 2014047540 A1 | 3/2014 |
| WO | 2014124087 A1 | 8/2014 |
| WO | 2015143342 A1 | 9/2015 |
| WO | 2015179822 A1 | 11/2015 |
| WO | 2016103269 A1 | 6/2016 |
| WO | 2017132596 A1 | 8/2017 |
| WO | WO-2017173064 A1 * | 10/2017 ............ A61K 35/30 |
| WO | 2018053210 A1 | 3/2018 |
| WO | 2020061371 A2 | 3/2020 |

OTHER PUBLICATIONS

Gomez-Puerto et al. Bone morphogenetic protein receptor signal transduction in human disease. J Pathol 247: 9-20. (Year: 2019).*
Bergles et al. Oligodendrocyte Development and Plasticity. Cold Spring Harb Perspect Biol 8: 1-27. (Year: 2016).*
Zhang et al. An RNA-Sequencing Transcriptome and Splicing Database of Glia, Neurons, and Vascular Cells of the Cerebral Cortex . The Journal of Neuroscience 34: 11929-11947. (Year: 2014).*
Sharifi et al. FABP7 expression in normal and stab-injured brain cortex and its role in astrocyte proliferation. Histochem Cell Biol 136: 501-513. (Year: 2011).*
Zhang et al. Pax6 Is a Human Neuroectoderm Cell Fate Determinant. Cell Stem Cell 7: 90-100. (Year: 2010).*
Eze Supplemental Information. Single-cell atlas of early human brain development highlights heterogeneity of human neuroepithelial cells and early radial glia Nature Neuroscience 24. 584-594. (Year: 2021).*
Tailor et al. Stem Cells Expanded from the Human Embryonic Hindbrain Stably Retain Regional Specification and High Neurogenic Potency. The Journal of Neuroscience 33: 12407-12422. (Year: 2013).*
Bian et al. Sequential Differentiation of Embryonic Stem Cells into Neural Epithelial-Like Stem Cells and Oligodendrocyte Progenitor Cells. PLoS One 11: 1-15. (Year: 2016).*
Abecasis et al. Expansion of 3D human induced pluripotent stem cell aggregates in bioreactors: Bioprocess intensification and scaling-up approaches. Journal of Biotechnology 246: 81-93. (Year: 2017).*
Eze et al. Single-cell atlas of early human brain development highlights heterogeneity of human neuroepithelial cells and early radial glia Nature Neuroscience 24. 584-594. (Year: 2021).*
Medina-Rodriguez et al. Protocol to Isolate a Large Amount of Functional Oligodendrocyte Precursor Cells from the Cerebral Cortex of Adult Mice and Humans. PLoS One 8: 1-13. (Year: 2013).*
Xue et al. Proliferation, multipotency and neuronal differentiation of cryopreserved neural progenitor cells derived from the olfactory neuroepithelium of the adult rat. Cell Biology International 32: 950-958. (Year: 2008).*
Yu et al. ERK inhibition promotes neuroectodermal precursor commitment by blocking self-renewal and primitive streak formation of the epiblast. Stem Cell Research & Therapy 9: 1-13. (Year: 2018).*
Abiraman et al. Anti-Muscarinic Adjunct Therapy Accelerates Functional Human Oligodendrocyte Repair. The Journal of Neuroscience 35:3676-3688. (Year: 2015).*

(56) References Cited

OTHER PUBLICATIONS

Xue et al. Mechanics-guided embryonic patterning of neuroectoderm tissue from human pluripotent stem cells. Nature Materials 17: 633-641. 2018; published Jul. 2018 (Year: 2018).*
Liu et al. Microfibrous carriers for integrated expansion and neural differentiation of embryonic stem cells in suspension bioreactor. Biochemical Engineering Journal 75: 55-63. (Year: 2013).*
Nothias et al. (2005) "Combined Effects of Neurotrophin Secreting Transplants, Exercise, and Serotonergic Drug Challenge Improve Function In Spinal Rats", Neurorehabilitation and Neural Repair, 19(4):296-312.
Orentas et al. (Jun. 1999) "Sonic Hedgehog Signaling is Required During the Appearance of Spinal Cord Oligodendrocyte Precursors", Development, 126(11):2419-2429.
Roy et al. (Oct. 22, 2006) "Functional Engraftment of Human ES Cell-Derived Dopaminergic Neurons Enriched by Coculture with Telomerase-Immortalized Midbrain Astrocytes", Nature Medicine, 12(11):1259-1268.
Scheff et al. (2003) "Experimental Modeling of Spinal Cord Injury: Characterization of a Force-Defined Injury Device", Journal of Neurotrauma, 20(2):179-193.
Sharp et al. (Jan. 2010) "Human Embryonic Stem Cell-Derived Oligodendrocyte Progenitor Cell Transplants Improve Recovery after Cervical Spinal Cord Injury", Stem Cells, 28(1):152-163.
Singh, Juhi (2018) "Role of PDGF-A Activated Intracellular Signalling in Oligodendrocyte Progenitor Migration", PhD Thesis, 153 pages.
Sokol, Sergei Y. (Oct. 2011) "Maintaining Embryonic Stem Cell Pluripotency with WNT Signaling", 138 (20):4341-4350.
Sundberg et al. (2010) "Production and Isolation of NG2+ Oligodendrocyte Precursors from Human Embryonic Stem Cells in Defined Serum-Free Medium", Stem Cell Research, 5(2):91-103.
Tang et al. (2014) "Redirection of Doublecortin-Positive Cell Migration by OverExpression of the Chemokines MCP-1, MIP-1 a and Gro-a in the Adult Rat Brain", Neuroscience, 260:240-248.
Totiou et al. (2005) "Spinal Cord Injury Is Accompanied by Chronic Progressive Demyelination", The Journal of Comparative Neurology, 486:373-383.
Vadivelu et al. (2015) "Ng2+ Progenitors Derived from Embryonic Stem Cells Penetrate Glial Scar and Promote Axonal Outgrowth Into White Matter After Spinal Cord Injury", Stem Cells Translational Medicine, 4(4):401-411.
Wang et al. (2014) "ApoE Mimetic Ameliorates Motor Deficit and Tissue Damage in Rat Spinal Cord Injury", Journal of Neuroscience Research, 92(7):884-892.
Wirth, E. (May 16, 2014) "Phase I Clinical Trial of Human Embryonic Stem Cell-Derived Oligodendrocyte Progenitors In Subjects with Neurologically Complete Thoracic Spinal Cord Injury: Results and Next Steps", American Spinal Injury Association (ASIA) 2014 Meeting, San Antonio, Texas, (Oral Presentation), 7 pages.
Wright et al. (2014) "Novel Roles for Osteopontin and Clusterin in Peripheral Motor and Sensory Axon Regeneration", Journal of Neuroscience, 34(5):1689-1700.
Zhang et al. (2018) "Highly Efficient Methods to Obtain Homogeneous Dorsal Neural Progenitor Cells From Human and Mouse Embryonic Stem Cells and Induced Pluripotent Stem Cells", Stem Cell Research and Therapy, 9(67):13 pages.
Zhang et al. (2006) "Oligodendrocyte Progenitor Cells Derived from Human Embryonic Stem Cells Express Neurotrophic Factors", Stem Cells and Development, 15(6):943-952.
Zhang et al. (Apr. 2011) "Role of Matrix Metalloproteinases and Therapeutic Benefits of Their Inhibition in Spinal Cord Injury", Neurotherapeutics, 8(2):206-220.
Hu et al. (Jul. 16, 2009) "Hepatocyte Growth Factor Enhances the Generation of High-purity Oligodendrocytes from Human Embryonic Stem Cells", Differentiation, 78(2-3):177-184.
Hu et al. (Mar. 2, 2010) "Neural Differentiation of Human Induced Pluripotent Stem Cells Follows Developmental Principles but with Variable Potency", Proc. Natl. Acad. Sci. U.S.A., 107(9):4335-4340.
(2018) Enhanced Proliferation of Primary Nscs and Sustained Differentiation Into Precursors Using Heat-stable bFGF, Gibco, 3 pages.
European Search Report issued in European Application Application No. 17851575.5, mailed on Mar. 24, 2020, 6 pages.
Extended European Search Report for Application No. EP 19862819.0, mailed on Jun. 10, 2022, 11 pages.
Extended European search report for EP Application No. 20745781.3, mailed on Oct. 26, 2022, 8 Pages.
Extended European Search Report received for European Application No. 17776639.1, mailed on Sep. 26, 2019, 8 pages.
(2016) History of Changes for Study: NCT02302157, https://clinicaltrials.gov/ct2/history/NCT02302157?v_17=View#StudyPageTop, 5 pages.
International Preliminary Report on Patentability for International Application No. PCT/US2017/051677, Mailed on Mar. 28, 2019, 10 pages.
International Preliminary Report on Patentability for PCT Application No. PCT/US2017/24986, mailed on Oct. 11, 2018, 8 pages.
International Search Report and Written Opinion for PCT Application No. PCT/US2017/24986, mailed on Aug. 22, 2017, 11 pages.
International Search Report and Written Opinion issued in International Application No. PCT/US20/014834, mailed on Apr. 23, 2020, 11 Pages.
International Search Report and Written Opinion issued in International Application No. PCT/US2017/051677, Mailed on Dec. 4, 2017, 11 pages.
International Search Report and Written Opinion received for PCT Patent International Application No. PCT/US2022/014373, mailed on Jun. 30, 2022, 10 pages.
International Search Report and Written Opinion received for PCT Patent International Application No. PCT/US22/19847, Mailed on Jun. 27, 2022, 10 pages.
Alsanie et al. (2013) "Human Embryonic Stem Cell-Derived Oligodendrocytes: Protocols and Perspectives", Stem Cells and Development, 22(18):2459-2472.
Anderson et al. (Nov. 25, 2008) "Acceptable benefits and risks associated with surgically improving arm function in individuals living with cervical spinal cord injury", Spinal Cord, 47(4):334-338.
Armstrong et al. (Nov. 1990) "Type 1 Astrocytes and Oligodendrocyte-type 2 Astrocyte Glial Progenitors Migrate Toward Distinct Molecules", Journal of Neuroscience Research, 27(3):400-407.
Bain et al. (Apr. 1995) "Embryonic Stem Cells Express Neuronal Properties in Vitro", Developmental Biology, 168:342-357.
Bansod et al. (2017) "Hes5 Regulates the Transition Timing of Neurogenesis and Gliogenesis in Mammalian Neocortical Development", Development, 3156-3167.
Behrmann et al. (1992) "Spinal Cord Injury Produced by Consistent Mechanical Displacement of the Cord in Rats: Behavioral and Histologic Analysis", Journal of Neurotrauma, 9(3):197-217.
Briscoe et al. (Jun. 2001) "A Hedgehog-insensitive Form of Patched Provides Evidence for Direct Long-range Morphogen Activity of Sonic Hedgehog in the Neural Tube", Molecular Cell, 7(6):1279-1291.
Cai et al. (Jan. 6, 2005) "Generation of Oligodendrocyte Precursor Cells from Mouse Dorsal Spinal Cord Independent of Nkx6 Regulation and Shh Signaling", Neuron, 41-53.
Cao et al. (Jan. 2001) "Pluripotent Stem Cells Engrated into the Normal or Lesioned Adult Rat Spinal Cord Are Restricted to a Glial Lineage", Experimental Neurology, 167(1):48-58.
Chapman et al. (Sep. 2012) "Evaluating the First-in-human Clinical Trial of a Human Embryonic Stem Cell-based Therapy", Kennedy Institute of Ethics Journal, 22(3):243-261.
Davies et al. (Mar. 2, 2011) "Transplantation of Specific Human Astrocytes Promotes Functional Recovery after Spinal Cord Injury", Plos One, e17328, 6(3):13 pages.
Doi et al. (Feb. 10, 2012) "Prolonged Maturation Culture Favors a Reduction in the Tumorigenicity and the Dopaminergic Function of Human ESC-Derived Neural Cells in a Primate Model of Parkinson's Disease", Stem Cells, 30(5):935-945.

(56) References Cited

OTHER PUBLICATIONS

Douvaras et al. (Aug. 12, 2014) "Efficient Generation of Myelinating Oligodendrocytes from Primary Progressive Multiple Sclerosis Patients by Induced Pluripotent Stem Cells", Stem Cell Reports, 3(2):250-259.
Douvaras et al. (Jul. 2, 2015) "Generation and Isolation of Oligodendrocyte Progenitor Cells From Human Pluripotent Stem Cells", Nature Protocols, 10:143-1154.
Du et al. (2014) "Mechanism of SB431542 in Inhibiting Mouse Embryonic Stem Cell Differentiation", Cellular Signalling, 26(10):2107-2116.
Ericson et al. (Nov. 15, 1996) "Two Critical Periods of Sonic Hedgehog Signaling Required for the Specification of Motor Neuron Identity", Cell, 87(4):661-673.
Faulkner et al. (Dec. 2005) "Human Embryonic Stem Cell-Derived Oligodendrocyte Progenitors for the Treatment of Spinal Cord Injury", Transplant Immunology, 15(2):131-142.
Fuhrmann et al. (Jan. 1, 2016) "Injectable Hydrogel Promotes Early Survival of Induced Pluripotent Stem Cell-Derived Oligodendrocytes and Attenuates Longterm Teratoma Formation in a Spinal Cord Injury Model", Biomaterials, 83:23-36.
Goldman, Steven A. (Jul. 2005) "Stem and Progenitor Cell-based Therapy of the Human Central Nervous System", Nature Biotechnology, 23(7):862-871.
Gordon et al. (Jan. 2012) "Hemokines Influence The Migration And Fate Of Neural Precursor Cells From The Young Adult And Middle-aged Rat Subventricular Zone", Experimental Neurology, 233(1):587-594.
Hatch et al. (2009) "Derivation of High-Purity Oligodendroglial Progenitors", Methods in Molecular Biology, 549:59-75.
Hu et al. (Oct. 15, 2009) "Differentiation of Human Oligodendrocytes from Pluripotent Stem Cells", Nature Protocols, 4(11):1614-1622.
Hulsebosch et al. (Jan. 29, 2009) "Rodent Model of Chronic Central Pain After Spinal Cord Contusion Injury and Effects of Gabapentin", Journal of Neurotrauma, 17(12):1205-1217.
Karimi-Abdolrezaee et al. (Mar. 29, 2006) "Delayed Transplantation of Adult Neural Precursor Cells Promotes Remyelination and Functional Neurological Recovery After Spinal Cord Injury", Journal of Neuroscience, 26 (13):3377-3389.
Klimaschewski et al. (Nov. 2001) "Regulation of clusterin expression following spinal cord injury", Cell and Tissue Research, 306(2):209-216.
Kriks et al. (Nov. 6, 2011) "Dopamine Neurons Derived from Human ES Cells Efficiently Engraft In Animal Models of Parkinson's Disease", Nature, 480(7378):547-551.
Kuespert et al. (May 1, 2016) "Something 2 Talk About—Transcriptional Regulation In Embryonic And Adult Oligodendrocyte Precursors", Brain Research, 1638:16 pages.
Kurek et al. (Jan. 13, 2015) "Endogenous WNT Signals Mediate BMP-Induced and Spontaneous Differentiation of Epiblast Stem Cells and Human Embryonic Stem Cells", Stem Cell Reports, 4(1):114-28.
Li et al. (May 15, 2013) "Differentiation Of Oligodendrocyte Progenitor Cells From Human Embryonic Stem Cells On Vitronectin-Derived Synthetic Peptide Acrylate Surface", Stem Cells and Development, 22(10):1497-1505.
Lu et al. (2014) "Long-Distance Axonal Growth from Human Induced Pluripotent Stem Cells After Spinal Cord Injury", Neuron, 83(4):789-796.
Ma et al. (2009) "Oligodendrocyte Precursor Cells Differentially Expressing Noga-A but Not Mag Are More Permissive to Neurite Outgrowth Than Mature Oligodendrocytes", Experimental Neurology, 217(1):184-196.
Metz et al. (2000) "Validation of the Weight-Drop Contusion Model in Rats: A Comparative Study of Human Spinal Cord Injury", Journal of Neurotrauma, 17(1):1-17.
Mitsui et al. (2005) "Transplantation of Neuronal and Glial Restricted Precursors Into Contused Spinal Cord Improves Bladder and Motor Functions, Decreases Thermal Hypersensitivity, and Modifies Intraspinal Circuitry", Journal of Neuroscience, 25(42):9624-9636.

Nakamura et al. (Jun. 20, 2005) "Transplantation of Embryonic Spinal Cord-Derived Neurospheres Support Growth of Supraspinal Projections and Functional Recovery After Spinal Cord Injury in the Neonatal Rat", Journal of Neuroscience, 81(4):457-468.
Nemati et al. (2016) "Scalable Expansion of Human Pluripotent Stem Cell-Derived Neural Progenitors in Stirred Suspension Bioreactor Under Xeno-free Condition", Methods in Molecular Biology, 1502:143-58.
Nistor et al. (Feb. 2005) "Human Embryonic Stem Cells Differentiate into Oligodendrocytes in High Purity and Myelinate After Spinal Cord Transplantation", Glia, 49(3):385-396.
Noble et al. (2011) "Precursor Cell Biology and the Development of Astrocyte Transplantation Therapies: Lessons from Spinal Cord Injury", Neurotherapeutics, 8(4):677-693.
Chew et al. (2014) "Finding Degrees of Separation: Experimental Approaches for Astroglial and Oligodendroglial Cell Isolation and Genetic Targeting", Journal of Neuroscience Methods, 236:125-147 (23 pages).
Clausi et al. (2017) "Delayed ALK5 Inhibition Improves Functional Recovery in Neonatal Brain Injury", Journal of Cerebral Blood Flow and Metabolism, 37(3):787-800.
Kim et al. (2010) "Robust Enhancement of Neural Differentiation From Human ES and iPS Cells Regardless of Their Innate Difference in Differentiation Propensity", Stem cell reviews and reports, 6(2):270-281.
Lukovic et al. (2017) "Highly Efficient Neural Conversion of Human Pluripotent Stem Cells in Adherent and Animal-Free Conditions", Stem Cells Translational Medicine, 6(4):1217-1226.
Najm et al. (2011) "Rapid and Robust Generation of Functional Oligodendrocyte Progenitor Cells From Epiblast Stem Cells", Nature Methods, 8(11):957-962.
Ebrahimi-Barough et al. (Oct. 2013) "Differentiation of Human Endometrial Stromal Cells into Oligodendrocyte Progenitor Cells (OPCs)", Journal of Molecular Neuroscience, 51(2):265-273.
Gallo et al. (1995) "Developmental and Growth Factor-induced Regulation of Nestin in Oligodendrocyte Lineage Cells", Journal of Molecular Neuroscience, 15(1):394-406.
Shin et al. (Sep. 17, 2021) "Sensitive Timing of Undifferentiation in Oligodendrocyte Progenitor Cells and Their Enhanced Maturation in Primary Visual Cortex of Binocularly Enucleated Mice", PLoS One, 16(9):e0257395 (26 pages).
International Search Report and Written Opinion for International Application No. PCT/US2023/061506, mailed on Jul. 3, 2023, 13 pages.
Abbasalizadeh et al. (2012) "Bioprocess Development For Mass Production of Size-Controlled Human Pluripotent Stem Cell Aggregates in Stirred Suspension Bioreactor", Tissue Engineering: Part C Methods, 18(11):831-851.
Bardy et al. (Feb. 1, 2013) "Microcarrier Suspension Cultures for High-Density Expansion and Differentiation of Human Pluripotent Stem Cells to Neural Progenitor Cells". Tissue Engineering. Part C, Methods, 19(2):166-180.
Hu et al. (May 2009) "Human Oligodendrocytes From Embryonic Stem Cells: Conserved SHH Signaling Networks and Divergent FGF Effects", Development, 136(9):1443-1452.
Kimura et al. (2012) "Ultrasonographic Quantification of Spinal Cord and Dural Pulsations during Cervical Laminoplasty in Patients with Compressive Myelopathy", Eur, Spine J., 21(12):2450-2455.
Manley et al. (Oct. 2017) "Human Embryonic Stem Cell-Derived Oligodendrocyte Progenitor Cells: Preclinical Efficacy and Safety in Cervical Spinal Cord Injury", Stem Cells Translational Medicine, 6(10):1917-1929.
Munst et al. (2018) "In Vitro Segregation and Isolation of Human Pluripotent Stem Cell-Derived Neural Crest Cells", Methods, 133:65-80 (49 pages).
Ota et al. (Mar. 2006) "BMP and FGF-2 Regulate Neurogenin-2 Expression and the Differentiation of Sensory Neurons and Glia", Developmental Dynamics, 235(3):646-655.
Patthey et al. (Feb. 1, 2014) "Signaling Pathways Regulating Ectodermal Cell Fate Choices", Experimental Cell Research, 321(1):11-16.

(56) References Cited

OTHER PUBLICATIONS

Riemens et al. (Sep. 2018) "Directing Neuronal Cell Fate in Vitro: Achievements and Challenges", Progress in Neurobiology, 168:42-68 (130 pages).

Vigil et al. (Apr. 2008) "Efficacy of Tacrolimus In Inhibiting Inflammation Caused by Carrageenan in a Murine Model of Air Pouch", Transplant Immunology, 19(1):25-29.

Zheng et al. (Aug. 2018) Differentiation of Glial Cells From hiPSCs: Potential Applications in Neurological Diseases and Cell Replacement Therapy, Frontiers in Cellular Neuroscience, 12:239 (21 pages).

Fischer et al. (Jul. 2020) "Transplanting Neural Progenitor Cells To Restore Connectivity After Spinal Cord Injury", Nature Reviews Neuroscience, 21(7):366-383.

Zhou et al. (Apr. 2, 2014) "GSK3β Promotes the Differentiation of Oligodendrocyte Precursor Cells via β-Catenin-Mediated Transcriptional Regulation", Molecular Neurobiology, 50:507-519.

Franz, et al., "Motor Levels in High Cervical Spinal cord injuries: Implications for the International Standards for Neurological Classification of Spinal Cord Injury", The Journal of Spinal Cord Medicine 39(5), 513-517, 2016.

Ilic, Dusko, Latest Developments in the Field of Stem Cell Research and Regenerative Medicines Regenerative Medicine', 9(6):713-719., Nov. 28, 2014.

Marcantonini, et al., "Natural Cryoprotective and Cytoprotective Agents in Cryopreservation: A Focus on Melatonin Molecules", 27(10):3254 (pp. 1-17)., May 19, 2022.

Milosevic, et al., "Cryopreservation Does Not Affect Proliferation And Multipotency Of Murine Neural Precursor Cells", Stem Cells, 23(5):681-688., May 2005.

Raju, et al., "The Need For Novel Cryoprotectants And Cryopreservation Protocols: Insights Into The Importance Of Biophysical Investigation And Cell Permeability", Biochimica et Biophysica Acta (BBA)—General Subjects, 1865 (1): 129749 (pp. 1-11). Jan. 2021.

Stylianou, et al., "Novel Cryoprotectant Significantly Improves the Post-thaw Recovery and Quality of HSC from CB", Cytotherapy 8(1):57-61., 2006.

\* cited by examiner

METHODS FOR DIFFERENTIATING PLURIPOTENT STEM CELLS IN DYNAMIC SUSPENSION CULTURE

FIELD

The present disclosure relates to the field of cell biology and neuroectoderm and glial lineage cells, such as oligodendrocyte progenitor cells. More specifically, the disclosure relates to novel methods for differentiating pluripotent stem cells to neuroectoderm in dynamic suspension culture using small molecule or protein inhibitors of TGFP/Activin/Nodal signaling and BMP signaling. The present disclosure further provides novel methods for differentiating pluripotent stem cells such as human embryonic stem cells first to neuroectoderm, then further to glial progenitor cells, and further to oligodendrocyte progenitor cells. The present disclosure further relates to neuroectoderm cells, glial progenitor cells and oligodendrocyte progenitor cells produced by the methods according to the invention that express one or more markers.

BACKGROUND

Oligodendrocyte progenitor cells (OPCs) are a subtype of glial cells in the central nervous system (CNS) that mature into myelin-producing oligodendrocytes. Oligodendrocytes produce the myelin sheath that insulates neuronal axons and remyelinate CNS lesions where the myelin sheath has been lost. Oligodendrocytes also contribute to neuroprotection through other mechanisms, including production of neurotrophic factors that promote neuronal survival (Wilkins A, Chandran S, Compston A. A role for oligodendrocyte-derived IGF-1 in trophic support of cortical neurons. 2001 *Glia.* 36 (1):48-57; Dai X, Lercher L D, Clinton P M, Du Y, Livingston D L, Vieira C, Yang L, Shen M M, Dreyfus C F. The trophic role of oligodendrocytes in the basal forebrain. 2003 *J Neurosci.* 23 (13):5846-53; Du Y, Dreyfus C F. Oligodendrocytes as providers of growth factors. 2002 *J Neurosci Res.* 68 (6):647-54). Accordingly, oligodendrocytes are an important therapeutic target for demyelinating and dysmyelinating disorders (such as multiple sclerosis, adrenoleukodystrophy and adrenomyeloneuropathy), other neurodegenerative disorders (such as Alzheimer's disease, amyotrophic lateral sclerosis, and Huntington's disease) and acute spinal cord injury (SCI).

OPCs are derived from neuroectoderm (also known as neural ectoderm or neural tube epithelium), which gives rise to neural progenitors that will generate the various neurons and glial cells that comprise the CNS. Several methods have been developed for differentiation of human pluripotent stem cells such as embryonic stem cells (ESCs) and induced pluripotent stem cells (iPSCs) into OPCs that can be used in cellular therapy. For the initial step of induction to neuroectoderm lineage cells and neural progenitor cells, most of the existing protocols rely on formation of embryoid bodies (EBs) and subsequently, neurospheres in static non-adherent culture in the presence of the caudalizing agent retinoic acid (Nistor G I, Totoiu M O, Haque N, Carpenter M K, Keirstead H S. Human embryonic stem cells differentiate into oligodendrocytes in high purity and myelinate after spinal cord transplantation. 2005 *Glia.* 49 (3):385-96; Izrael M, Zhang P, Kaufman R, Shinder V, Ella R, Amit M, Itskovitz-Eldor J, Chebath J, Revel M. Human oligodendrocytes derived from embryonic stem cells: Effect of noggin on phenotypic differentiation in vitro and on myelination in vivo. 2007 *Mol. Cell. Neurosci.* 34: 310-323; Hu B Y, Du Z W, Zhang S C. Differentiation of human oligodendrocytes from pluripotent stem cells. 2009 *Nat. Protoc.* 4:1614-1622). Alternative differentiation protocols under adherent conditions have also been reported (Hu Z, Li T, Zhang X, Chen Y. Hepatocyte growth factor enhances the generation of high-purity oligodendrocytes from human embryonic stem cells. 2009 *Differentiation.* 78: 117-184). Both EB-based and adherent differentiation protocols require manual selection of the neural precursors to optimize yields and are not easily scalable, limiting their usefulness for making large quantities of therapy-grade cells. Additionally, small numbers of cell types outside of the neuroectoderm lineage are able to persist during the differentiation process and contribute to undesirable cell types in the final OPC population, including, for example, epithelial cells or chondrocyte progenitor cells (Manley N C, Priest C A, Denham J, Wirth E D 3rd, Lebkowski J S. Human Embryonic Stem Cell-Derived Oligodendrocyte Progenitor Cells: Preclinical Efficacy and Safety in Cervical Spinal Cord Injury. *Stem Cells Transl Med.* 2017 October; 6 (10):1917-1929).

More recently, methods have been developed that improve the efficiency of neural induction (neuroectoderm formation) by the use of inhibitors of transforming growth factor beta (TGFB)/Activin/Nodal signaling concurrently with inhibitors of bone morphogenetic protein (BMP) signaling. This process, also known as dual SMAD inhibition, has been shown to promote efficient differentiation of human embryonic stem cells into neuroectoderm lineage cells (Chambers S M, Craft C A, Papapetrou E P, Tomishima M, Sadelain, M. Studer, L. Highly efficient neural conversion of human ES and iPS cells by dual inhibition of SMAD signaling. 2009 *Nat Biotechnol.* 27 (3):275-280). In the standard dual SMAD inhibition protocol, neural induction and subsequent steps of the differentiation are performed on adherent monolayer culture, eliminating the highly heterogeneous cell populations generated by EB-based neural induction methods and minimizing non-neural cells. This method has been successfully used to generate glial progenitor cells and OPCs from pluripotent stem cells (Douvaras P, Wang J, Zimmer M, Hanchuk S, O'Bara M A, Sadiq S, Sim F J, Goldman J, Fossati V. Efficient generation of myelinating oligodendrocytes from primary progressive multiple sclerosis patients by induced pluripotent stem cells. 2014 *Stem Cell Reports.* 3 (2):250-9). However, one disadvantage of adherent monolayer culture is its limited scalability and yield compared to three-dimensional (3D) culture methods. Moreover, 3D culture environments mimic the natural cellular microenvironment; it is thought that cells gown using a 3D cell culture technique more closely resemble natural tissues and organs than cells grown in (2D) adherent monolayers. Finally, adherent monolayer culture relies on the use of undefined ingredients and animal-derived components, such as Matrigel® and knockout serum replacement (KSR).

To address these limitations, methods combining the dual SMAD inhibition with EB formation have been recently developed and tested (Kirkeby A, Grealish S, Wolf D A, Nelander J, Wood J, Lundblad M, Lindvall O, Parmar M. Generation of regionally specified neural progenitors and functional neurons from human embryonic stem cells under defined conditions. 2012 *Cell Rep.* 1 (6):703-14; Crompton L A, Byrne M L, Taylor H, Kerrigan T L, Bru-Mercier G, Badger J L, Barbuti P A, Jo J, Tyler S J, Allen S J, Kunath T, Cho K, Caldwell M A. Stepwise, non-adherent differentiation of human pluripotent stem cells to generate basal forebrain cholinergic neurons via hedgehog signaling. 2013 *Stem Cell Res.* 11 (3):1206-21; Pauly M G, Krajka V, Stengel F, Seibler P, Klein C, Capetian P. Adherent vs. Free-Floating Neural Induction by Dual SMAD Inhibition for Neurosphere Cultures Derived from Human Induced Pluripotent Stem Cells. 2018 *Front Cell Dev Biol.* 6:3). In the EB-based methods, small molecule inhibitors of TGFβ/Activin/Nodal signaling and BMP signaling are applied to EBs formed in static non-adherent culture. However, EB-based dual SMAD inhibition is not easily scalable for the production of large quantities of targeted cells and results in greater degree of variability in the obtained cells, in part because the static culture of the EBs results in different size aggregates being formed and requires frequent trituration throughout the process (Crompton L A, Byrne M L, Taylor H, Kerrigan T L, Bru-Mercier G, Badger J L, Barbuti P A, Jo J, Tyler S J, Allen S J, Kunath T, Cho K, Caldwell M A. Stepwise, non-adherent differentiation of human pluripotent stem cells to generate basal forebrain cholinergic neurons via hedgehog signaling. 2013 *Stem Cell Res.* 11 (3):1206-21).

There is a need for improved methods for differentiating pluripotent stem cells into neuroectoderm and further to glial progenitor cells and OPCs. Ideally, such methods should be easily scalable to produce sufficient quantities of differentiated cells for cell therapy applications while consistently and reproducibly producing the targeted cell types.

SUMMARY

In various embodiments described herein, the present disclosure provides, inter alia, robust, reliable protocols for differentiating human pluripotent stem cells such as ESCs and iPSCs into neuroectoderm and glial cells in dynamic suspension culture that can be performed in bioreactors and adapted to large scale culture. Also provided are protocols for differentiating human pluripotent stem cells to OPCs by inducing differentiation to neuroectoderm and further to glial cells in dynamic suspension culture, and subsequently differentiating the glial cells into OPCs.

The present disclosure is based, in part, on the discovery that the starting material pluripotent stem cells can be aggregated in dynamic suspension into non-EB aggregates wherein the pluripotent stem cells remain undifferentiated and subsequently, the aggregates can be induced to differentiate into neuroectoderm while in dynamic suspension by using one or more inhibitors of TGFβ/Activin/Nodal signaling and one or more inhibitors of BMP signaling. Differentiating pluripotent stem cells in dynamic suspension in accordance with the present disclosure provides a scalable, reproducible and controllable process for producing large quantities of targeted neuroectoderm lineage cells from the starting material, in contrast with adherent culture and EB-based methods.

The methods of the present disclosure reproducibly produce neuroectoderm progenitor cells by day 7 of the differentiation process, glial progenitor cells by day 21 of the differentiation process and OPCs by day 42 of the differentiation process. The Day 42 OPCs produced in accordance with the present disclosure are comparable (in terms of their overall marker expression profile) to OPCs generated using an alternative method that are currently in clinical testing to treat spinal cord injury (Priest C A, Manley N C, Denham J, Wirth E D 3rd, Lebkowski J S. Preclinical safety of human embryonic stem cell-derived oligodendrocyte progenitors supporting clinical trials in spinal cord injury. *Regen Med.* 2015 November; 10 (8):939-58; Manley N C, Priest C A, Denham J, Wirth E D 3rd, Lebkowski J S. Human Embryonic Stem Cell-Derived Oligodendrocyte Progenitor Cells: Preclinical Efficacy and Safety in Cervical Spinal Cord Injury. *Stem Cells Transl Med.* 2017 October; 6 (10):1917-1929), with the exception that the OPCs produced in accordance with present disclosure express lower levels of non-OPC markers, including markers associated with epithelial cyst formation in vitro.

In one embodiment, the present disclosure provides a method of obtaining a population of cells comprising glial progenitor cells from undifferentiated human pluripotent stem cells. In certain embodiments, the method comprises: (a) obtaining a suspension culture of non-embryoid body (non-EB) aggregates of undifferentiated human pluripotent stem cells, wherein the human pluripotent stem cells remain in an undifferentiated state; (b) culturing the non-EB aggregates from (a) in dynamic suspension in the presence of at least one inhibitor of transforming growth factor beta (TGFβ/Activin/Nodal signaling and at least one inhibitor of bone morphogenetic protein (BMP) signaling for a first time period, thereby inducing differentiation to neuroectoderm; (c) culturing the non-EB aggregates from (b) in dynamic suspension in the presence of retinoic acid and at least one agonist of Smoothened receptor for a second time period; and (d) culturing the aggregates from (c) in dynamic suspension in the presence of basic fibroblast growth factor (bFGF) and epidermal growth factor (EGF) for a further time period, until the cells have matured into glial progenitor cells.

In certain embodiments, the first time period is about three to four days. In certain embodiments, the second time period is about four days. In certain embodiments, steps (a) and (b) are performed over a period of about seven to eight days. In certain embodiments, steps (a) through (d) are performed over a period of about twenty-one days.

In certain embodiments, the method further comprises an additional step of harvesting the non-EB aggregates from (d) and plating them onto a substrate, thereby resulting in migration of cells out from the aggregates. In certain embodiments, the substrate is a cell adhesion peptide. In other embodiments, the substrate is an extracellular matrix protein. In certain embodiments, the substrate is recombinant human laminin-521. In other embodiments, the substrate is vitronectin or laminin-511 E8 fragment. In yet other embodiments, the substrate is a synthetic substrate, such as, for example, Synthemaxe®-II SC Substrate.

In further embodiments, the method comprises an additional step of culturing the cells that have migrated out of the aggregates adherently on a substrate in the presence of epidermal growth factor (EGF) and platelet derived growth factor AA (PDGF-AA) for a further time period until the cells have matured into OPCs. In certain embodiments, the substrate is a cell adhesion peptide. In other embodiments, the substrate is an extracellular matrix protein. In certain embodiments, the substrate is recombinant human laminin-521. In other embodiments, the substrate is vitronectin or laminin-511 E8 fragment. In certain embodiments, the adherent culturing is performed for about 21 days.

In another embodiment, the present disclosure provides a method of inducing differentiation of human pluripotent stem cells into neuroectoderm cells, the method comprising: (a) obtaining a suspension culture of non-embryoid body (non-EB) aggregates of undifferentiated human pluripotent stem cells, wherein the human pluripotent stem cells remain in an undifferentiated state; (b) culturing the non-EB aggregates from (a) in dynamic suspension in the presence of at least one inhibitor of transforming growth factor beta (TGFβ/Activin/Nodal signaling and at least one inhibitor of bone morphogenetic protein (BMP) signaling for a first time period, thereby inducing differentiation to neuroectoderm;

and (c) culturing the non-EB aggregates from (b) in dynamic suspension in the presence of retinoic acid and at least one agonist of Smoothened receptor for a second time period; until the cells have matured into paired box 6 (PAX6) positive neuroectoderm cells.

In certain embodiments, the first time period is about three to four days. In certain embodiments, the second time period is about four days. In certain embodiments, steps (a) through (c) are performed over a period of about seven to eight days.

In an additional embodiment, the present disclosure provides a method of obtaining a population of cells comprising glial progenitor cells from undifferentiated human pluripotent stem cells, the method comprising: (a) culturing undifferentiated human pluripotent stem cells that have been disaggregated and form a single-cell suspension in dynamic suspension to obtain non-embryoid body (non-EB) aggregates, wherein the human pluripotent stem cells in the non-EB aggregates remain in an undifferentiated state; (b) culturing the non-EB aggregates from (a) in dynamic suspension in the presence of at least one inhibitor of transforming growth factor beta (TGFβ/Activin/Nodal signaling and at least one inhibitor of bone morphogenetic protein (BMP) signaling for a first time period, thereby inducing differentiation to neuroectoderm; (c) culturing the non-EB aggregates from (b) in dynamic suspension in the presence of retinoic acid and at least one agonist of Smoothened receptor for a second time period; and (d) culturing the aggregates from (c) in dynamic suspension in the presence of basic fibroblast growth factor (bFGF) and epidermal growth factor (EGF) for a further time period, until the cells have matured into glial progenitor cells.

In certain embodiments, the at least one inhibitor of TGFP/Activin/Nodal signaling is an inhibitor of activin receptor-like kinase 5 (ALK5). In other embodiments, the at least one inhibitor of TGFP/Activin/Nodal signaling is selected from the group consisting of SB431542, LY2157299, GW788388, A-77-01, A-83-01 and SB505124. In yet other embodiments, the inhibitor of TGFP/Activin/Nodal signaling is SB431542.

In certain embodiments, the at least one inhibitor of BMP signaling is an inhibitor of activin receptor-like kinase 2 (ALK2). In other embodiments, the at least one inhibitor of BMP signaling is selected from the group consisting of Dorsomorphin, DMH-1, K02288, ML3467, LDN193189 and Noggin protein. In yet other embodiments, the inhibitor of BMP signaling is Dorsomorphin.

In certain embodiments, the at least one Smoothened receptor agonist is selected from the group consisting of Purmorphamine, Smoothened Agonist (SAG, CAS 364590-63-6) and Sonic Hedgehog (SHH) protein. In yet other embodiments, the Smoothened receptor agonist is Purmorphamine.

An additional embodiment is a differentiated cell population comprising PAX6 positive neuroectoderm cells obtained according to the methods of the present disclosure. In certain embodiments, the PAX6 positive neuroectoderm cells further express one or more markers selected from HESS and ZBTB16.

Another embodiment is a differentiated cell population comprising glial progenitor cells obtained according to methods of the present disclosure. In certain embodiments, the glial progenitor cells express one or more markers selected from calcium voltage-gated channel auxiliary subunit gamma 4 (CACNG4), fatty acid binding protein 7 (FABP7), and sex determining region Y-box 6 (SOX6).

A yet another embodiment is a differentiated cell population comprising OPCs obtained according to methods of the present disclosure. In a preferred embodiment, the OPCs produced according to the methods according to the invention express one or more markers selected from neural/glial antigen 2 (NG2), platelet-derived growth factor receptor A (PDGFRα) and ganglioside GD3 (GD3) (GD3 is also known as anti-disialoganglioside and Ganglioside GD3 Synthase). So, for example, OPCs prepared according to the invention can express NG2, PDGFRα, or GD3; a combination of NG2 and PDGFRαa, NG2 and GD3, or PDGFRα and GD3; or a combination of NG2, PDGFRα and GD3. In certain embodiments, the differentiated cell population comprises at least 60% of cells that are NG2 positive. In certain embodiments, the differentiated cell population comprises at least 70% of cells that are NG2 positive. In certain embodiments, the differentiated cell population comprises at least 80% of cells that are NG2 positive. In other embodiments, the differentiated cell population comprises at least 90% of cells that are NG2 positive. In certain embodiments, the differentiated cell population comprises at least 98% of cells that are NG2 positive. In certain embodiments, the differentiated cell population comprises at least 60% of cells that are PDGFRα positive. In certain embodiments, the differentiated cell population comprises at least 70% of cells that are PDGFRα positive. In certain embodiments, the differentiated cell population comprises at least 80% of cells that are PDGFRα positive. In other embodiments, the differentiated cell population comprises at least 90% of cells that are PDGFRα positive. In certain embodiments, the differentiated cell population comprises at least 98% of cells that are PDGFRα positive. In certain embodiments, the differentiated cell population comprises at least 60% of cells that are GD3 positive. In certain embodiments, the differentiated cell population comprises at least 70% of cells that are GD3 positive. In certain embodiments, the differentiated cell population comprises at least 80% of cells that are GD3 positive. In other embodiments, the differentiated cell population comprises at least 90% of cells that are GD3 positive. In certain embodiments, the differentiated cell population comprises at least 98% of cells that are GD3 positive.

DETAILED DESCRIPTION

Figure 1:
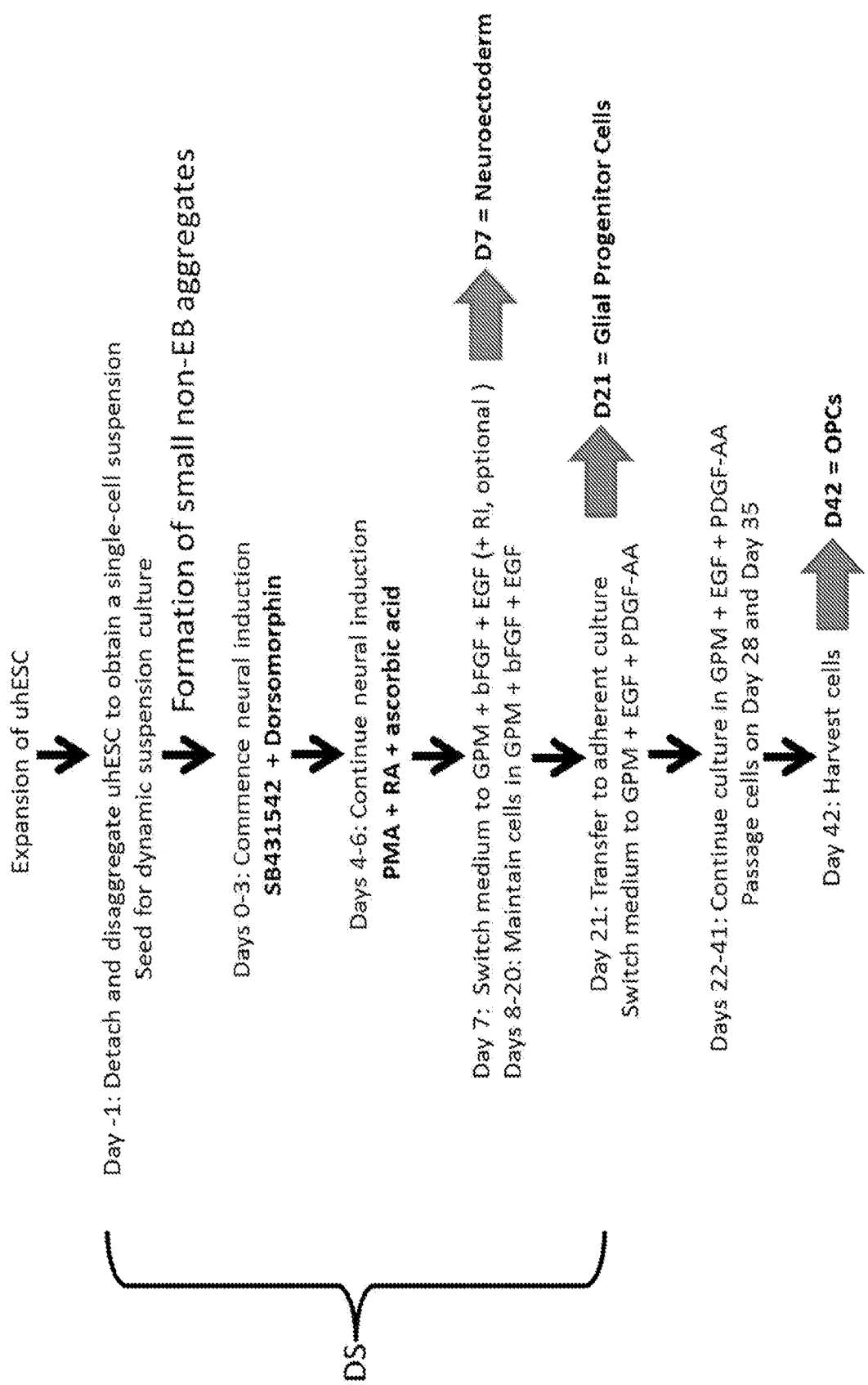
FIG. 1 is a diagram depicting differentiation of human embryonic stem cells to neuroectoderm (day 7) and further to glial progenitor cells (day 21) and oligodendrocyte progenitor cells (day 42) in accordance with the present disclosure. DS=dynamic suspension. Several additional small molecule inhibitors of TGFβ/Activin/Nodal signaling (other than SB431542) and BMP signaling (other than Dorsomorphin) were tested and were found to work equally well in the induction of differentiation to neuroectoderm (Example 7).

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to affect a disavowal of any part of the full scope of the invention. Hence, the following descriptions are intended to illustrate some particular aspects of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular embodiments only and is not intended to be limiting of the disclosure.

All publications, patent applications, patents and other references cited herein are incorporated by reference in their entireties.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

Methods disclosed herein can comprise one or more steps or actions for achieving the described method. The method steps and/or actions may be interchanged with one another without departing from the scope of the present invention. In other words, unless a specific order of steps or actions is required for proper operation of the aspect, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a percentages, density, volume and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, "oligodendrocyte progenitor cells" (OPCs) refer to cells found in the central nervous system that are of a neuroectoderm/glial lineage, express the characteristic marker neural/glial antigen 2 (NG2) and are capable of differentiating into oligodendrocytes. The OPCs prepared according to the methods of the invention may also express one or more of the markers selected from NG2, PDGFRα and GD3.

The terms "glial lineage cells," "glial progenitor cells" and "glial cells" are used interchangeably herein and refer to non-neuronal CNS cells that are derived from neuroectoderm/neural progenitor cells. Glial progenitor cells can be further differentiated to form OPCs/oligodendrocytes or astrocytes. In certain embodiments, the glial progenitor cells of the present disclosure express one or more markers selected from calcium voltage-gated channel auxiliary subunit gamma 4 (CACNG4), fatty acid binding protein 7 (FABP7), and sex determining region Y-box 6 (SOX6).

The terms "neuroectoderm," "neuroectoderm cells," "neuroectoderm precursor," "neuroectoderm progenitor," "neural progenitor" and "neural precursor" are used interchangeably herein and refer to cells that can be differentiated along a neural precursor pathway and that are capable of forming CNS neurons, oligodendrocytes, astrocytes and ependymal cells. In certain embodiments, the neuroectoderm cells of the present disclosure express one or more markers selected from paired box 6 (PAX6), Hes family BHLH transcription factor 5 (HESS) and zinc finger and BTB domain containing 16 (ZBTB16).

As used herein, the term "embryoid body" (EB) refers to a three-dimensional cellular aggregate derived from pluripotent stem cells that has undergone spontaneous differentiation towards all three germ layers. EBs are formed when pluripotent stem cells are removed from culture conditions that inhibit differentiation. For example, in the case of human embryonic stem cells, removal of basic fibroblast growth factor (bFGF) and transforming growth factor beta (TGFβ) from the culture media results in spontaneous differentiation towards all three germ layers and formation of EBs.

As used herein, the term "non-embryoid body aggregate" refers to a three-dimensional cellular aggregate formed from pluripotent stem cells where the pluripotent stem cells remain undifferentiated. In the present disclosure, non-EB aggregates are formed in dynamic suspension under cell culture conditions that maintain pluripotency and inhibit spontaneous differentiation (i.e., bFGF and TGFβ are not removed from the medium). Subsequently, the undifferentiated cellular aggregates are directed towards neuroectoderm progenitor cells by the simultaneous removal of bFGF and TGFP and addition of neuroectoderm differentiation factors, such as an inhibitor of the TGFP/Activin/Nodal signaling pathway combined with an inhibitor of the bone morphogenic protein signaling pathway.

As used herein, the term "TGFβ/Activin/Nodal signaling inhibitor" refers to a small molecule or protein modulator that is capable of downregulating signaling along the transforming growth factor beta (TGFβ)/Activin/Nodal signaling pathway. In certain embodiments, the TGFP/Activin/Nodal signaling inhibitor directly targets TGFβ type 1 receptor (TGFβR1), also known as activin receptor-like kinase 5 (ALK5). In certain embodiments, the TGFβ/Activin/Nodal signaling inhibitor is selected from the group consisting of SB431542, LY2157299, GW788388, A-77-01, A-83-01 and SB505124.

As used herein, the term "BMP signaling inhibitor" refers to a small molecule or protein modulator that is capable of downregulating signaling along the bone morphogenetic protein (BMP) signaling pathway. In certain embodiments, the BMP signaling inhibitor directly targets Activin A receptor, type I (ACVR1), also known as activin receptor-like kinase 2 (ALK2). In certain embodiments, the BMP signaling inhibitor is selected from the group consisting of Dorsomorphin, DMH-1, K02288, ML3467, LDN193189 and Noggin protein.

As used herein, the term "Smoothened agonist" or "Smoothened receptor agonist" refers to a small molecule or protein modulator that is capable of directly binding to and activating the G-protein coupled receptor Smoothened, which is part of the Sonic Hedgehog (SHH) signaling pathway. In certain embodiments, Smoothened receptor agonist is selected from the group consisting of Purmorphamine, Smoothened Agonist (SAG, CAS 364590-63¬6) and Sonic Hedgehog (SHH) protein.

As used herein, the term "undesirable cell types" refers to cells outside of the neuroectoderm lineage that can result in the formation of ectopic tissues upon implantation, or that result in the formation of one or more cysts in a cyst assay, as described herein. In an embodiment, "undesirable cell types" can include epithelial lineage cells such as cells positive for CD49f, a marker expressed by both neural progenitor cells and epithelial cells, or cells positive for CLDN6 or EpCAM, two markers expressed by both pluripotent cells and epithelial cells.

As used herein, "implantation" or "transplantation" refers to the administration of a cell population into a target tissue using a suitable delivery technique, (e.g., using an injection device).

As used herein, a "subject" refers to an animal or a human.

As used herein, a "subject in need thereof" refers to an animal or a human having damaged tissue in the central nervous system. In an embodiment, an animal or a human is experiencing a loss of motor function.

The terms "central nervous system" and "CNS" as used interchangeably herein refer to the complex of nerve tissues that control one or more activities of the body, which include but are not limited to, the brain and the spinal cord in vertebrates.

As used herein, "treatment" or "treating," with respect to a condition or a disease, is an approach for obtaining beneficial or desired results including preferably clinical results after a condition or a disease manifests in a patient. Beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, prolonging survival, and any combination thereof. Likewise, for purposes of this disclosure, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, prolonging survival, and any combination thereof.

Propagation and Culture of Undifferentiated Pluripotent Stem Cells

Differentiation of pluripotent stem cells in accordance with the present disclosure can be carried out using any suitable pluripotent stem cells as a starting material. In one embodiment, a method can be carried out on an human embryonic stem cell (hESC) line. In another embodiment, a method can be carried out using induced pluripotent stem cells (iPSCs). In another embodiment, a method can be carried out using cells that are derived from an H1, H7, H9, H13, or H14 cell line. In another embodiment, a method can be carried out on a primate pluripotent stem (pPS) cell line. In yet another embodiment, a method can be carried using undifferentiated stem cells derived from parthenotes, which are embryos stimulated to produce hESCs without fertilization.

Methods of propagation and culture of undifferentiated pluripotent stem cells have been previously described. With respect to tissue and cell culture of pluripotent stem cells, the reader may wish to refer to any of numerous publications available in the art, e.g., *Teratocarcinomas and Embryonic Stem cells: A Practical Approach* (E. J. Robertson, Ed., IRL Press Ltd. 1987); *Guide to Techniques in Mouse Development* (P. M. Wasserman et al., Eds., Academic Press 1993); *Embryonic Stem Cell Differentiation in vitro* (M. V. Wiles, Meth. Enzymol. 225:900, 1993); *Properties and Uses of Embryonic Stem Cells: Prospects for Application to Human Biology and Gene Therapy* (P. D. Rathjen et al., Reprod. Fertil. Dev. 10:31, 1998; and R. I. Freshney, Culture of Animal Cells, Wiley-Liss, New York, 2000).

Undifferentiated pluripotent stem cells can be maintained in an undifferentiated state without added feeder cells (see, e.g., (2004) Rosler et al., *Dev. Dynam.* 229:259). Feeder-free cultures are typically supported by a nutrient medium containing factors that promote proliferation of the cells without differentiation (see, e.g., U.S. Pat. No. 6,800,480). In one embodiment, conditioned media containing such factors can be used. Conditioned media can be obtained by culturing the media with cells secreting such factors. Suitable cells include, but are not limited to, irradiated (4,000 Rad) primary mouse embryonic fibroblasts, telomerized mouse fibroblasts, or fibroblast-like cells derived from pPS cells (U.S. Pat. No. 6,642,048). Medium can be conditioned by plating the feeders in a serum free medium, such as knockout DMEM supplemented with 20% serum replacement and 4 ng/mL bFGF. Medium that has been conditioned for 1-2 days can be supplemented with further bFGF, and used to support pPS cell culture for 1-2 days (see. e.g., WO 01/51616; Xu et al., (2001) *Nat. Biotechnol.* 19:971).

Alternatively, fresh or non-conditioned medium can be used, which has been supplemented with added factors (like a fibroblast growth factor or forskolin) that promote proliferation of the cells in an undifferentiated form. Non-limiting examples include a base medium like X-VIVO™ 10 (Lonza, Walkersville, Md.) or QBSF™-60 (Quality Biological Inc. Gaithersburg, Md.), supplemented with bFGF at 40-80 ng/mL, and optionally containing SCF (15 ng/mL), or Flt3 ligand (75 ng/mL) (see, e.g., Xu et al., (2005) *Stem Cells* 23 (3):315). These media formulations have the advantage of supporting cell growth at 2-3 times the rate in other systems (see, e.g., WO 03/020920). In one embodiment, undifferentiated pluripotent cells such as hES cells, can be cultured in a media comprising bFGF and TGFβ. Non-limiting example concentrations of bFGF include about 80 ng/ml. Non-limiting example concentrations of TGFβ include about 0.5 ng/ml. In yet another embodiment, undifferentiated pluripotent stem cells can be maintained in a commercially available, complete medium such as mTeSR™ (Stem Cell Technologies, Vancouver, Canada).

Undifferentiated pluripotent cells can be cultured on a layer of feeder cells, typically fibroblasts derived from embryonic or fetal tissue (Thomson et al. (1998) *Science* 282:1145). Feeder cells can be derived from a human or a murine source. Human feeder cells can be isolated from various human tissues, or can be derived via differentiation of human embryonic stem cells into fibroblast cells (see, e.g., WO 01/51616). Human feeder cells that can be used include, but are not limited to, placental fibroblasts (see, e.g., Genbacev et al. (2005) *Fertil. Stoll.* 83 (5):1517), fallopian tube epithelial cells (see, e.g., Richards et al. (2002) *Nat. Biotechnol.*, 20:933), foreskin fibroblasts (see, e.g., Amit et al. (2003) Biol. Reprod. 68:2150), and uterine endometrial cells (see, e.g., Lee et al. (2005) *Biol. Reprod.* 72 (1):42).

Various solid surfaces can be used in the culturing of undifferentiated pluripotent cells. Those solid surfaces include, but are not limited to, standard commercially available tissue culture flasks or cell culture plates, such as 6-well, 24-well, 96-well, or 144-well plates. Other solid surfaces include, but are not limited to, microcarriers and disks. Solid surfaces suitable for growing undifferentiated pluripotent cells can be made of a variety of substances including, but not limited to, glass or plastic such as polystyrene, polyvinylchloride, polycarbonate, polytetrafluorethylene, melinex, thermanox, or combinations thereof. Suitable surfaces can comprise one or more polymers, such as, e.g., one or more acrylates. A solid surface can be three-dimensional in shape. Non-limiting examples of three-dimensional solid surfaces have been previously described, e.g., in U.S. Patent Pub. No. 2005/0031598.

Undifferentiated stem cells can also be grown under feeder-free conditions on a growth substrate. A growth substrate can be a Matrigel® matrix (e.g., Matrigel®, Matrigel® GFR), recombinant laminin, laminin-511 recombinant fragment E8 or vitronectin. In certain embodiments of the present disclosure, the growth substrate is recombinant human laminin-521 (Biolamina, Sweden, distributed by Corning Inc., Corning, NY). In other embodiments, the substrate is a synthetic substrate, such as, for example, Synthemax®-II SC Substrate.

Undifferentiated stem cells can be passaged or subcultured using various methods such as using collagenase, or such as manual scraping. Undifferentiated stem cells can be subcultured by enzymatic means that generate a single cell suspension, such as using Accutase® (distributed by Sigma Aldrich, MO) or similar trypsinases. Alternatively, undifferentiated stem cells can be subcultured using non-enzymatic means, such as 0.5 mM EDTA in PBS, or such as using ReLeSR™ (Stem Cell Technologies, Vancouver, Canada).

In an embodiment, a plurality of undifferentiated stem cells are seeded or subcultured at a seeding density that allows the cells to reach confluence in about three to about ten days. In an embodiment, the seeding density can range from about $6.0 \times 10^3$ cells/cm$^2$ to about $5.0 \times 10^5$ cells/cm$^2$, such as about $1.0 \times 10^4$ cells/cm$^2$, such as about $5.0 \times 10^4$ cells/cm$^2$, such as about $1.0 \times 10^5$ cells/cm$^2$, or such as about $3.0 \times 10^5$ cells/cm$^2$ of growth surface. In another embodiment, the seeding density can range from about $6.0 \times 10^3$ cells/cm$^2$ to about $1.0 \times 10^4$ cells/cm$^2$ of growth surface, such as about $6.0 \times 10^3$ cells/cm$^2$ to about $9.0 \times 10^3$ cells/cm$^2$, such as about $7.0 \times 10^3$ cells/cm$^2$ to about $1.0 \times 10^4$ cells/cm$^2$, such as about $7.0 \times 10^3$ cells/cm$^2$ to about $9.0 \times 10^3$ cells/cm$^2$, or such as about $7.0 \times 10^3$ cells/cm$^2$ to about $8.0 \times 10^3$ cells/cm$^2$ of growth surface. In yet another embodiment, the seeding density can range from about $1.0 \times 10^4$ cells/cm$^2$ to about $1.0 \times 10^5$ cells/cm$^2$ of growth surface, such as about $2.0 \times 10^4$ cells/cm$^2$ to about $9.0 \times 10^4$ cells/cm$^2$, such as about $3.0 \times 10^4$ cells/cm$^2$ to about $8.0 \times 10^4$ cells/cm$^2$, such as about $4.0 \times 10^4$ cells/cm$^2$ to about $7.0 \times 10^4$ cells/cm$^2$, or such as about $5.0 \times 10^4$ cells/cm$^2$ to about $6.0 \times 10^4$ cells/cm$^2$ of growth surface. In an embodiment, the seeding density can range from about $1.0 \times 10^5$ cells/cm$^2$ to about $5.0 \times 10^5$ cells/cm$^2$ of growth surface, such as about $1.0 \times 10^5$ cells/cm$^2$ to about $4.5 \times 10^5$ cells/cm$^2$, such as about $1.5 \times 10^5$ cells/cm$^2$ to about $4.0 \times 10^5$ cells/cm$^2$, such as about $2.0 \times 10^5$ cells/cm$^2$ to about $3.5 \times 10^5$ cells/cm$^2$, or such as about $2.5 \times 10^5$ cells/cm$^2$ to about $3.0 \times 10^5$ cells/cm$^2$ of growth surface.

Any of a variety of suitable cell culture and sub-culturing techniques can be used to culture stem cells in accordance with the methods of the present disclosure. For example, a culture medium can be completely exchanged daily, initiating about 2 days after sub-culturing of the cells. In an embodiment, when a culture reaches about 90% colony coverage, cells can be detached and seeded for subsequent culture using one or more suitable reagents, such as, e.g., Accutase® to achieve a single cell suspension for quantification. In an embodiment, undifferentiated stem cells can then be sub-cultured before seeding the cells on a suitable growth substrate (e.g., recombinant human laminin-521) at a seeding density that allows the cells to reach confluence over a suitable period of time, such as, e.g., in about three to ten days. In one embodiment, undifferentiated stem cells can be subcultured using Collagenase IV and expanded on a recombinant laminin. In another embodiment, undifferentiated stem cells can be subcultured using Collagenase IV and expanded on a Matrigel®. In one embodiment, undifferentiated stem cells can be subcultured using ReLeSR™ and expanded on recombinant human laminin-521.

For seeding undifferentiated stem cells, the seeding density can range from about $6.0 \times 10^3$ cells/cm$^2$ to about $5.0 \times 10^5$ cells/cm$^2$, such as about $1.0 \times 10^4$ cells/cm$^2$, such as about $5.0 \times 10^4$ cells/cm$^2$, such as about $1.0 \times 10^5$ cells/cm$^2$, or such as about $3.0 \times 10^5$ cells/cm$^2$ of growth surface. In another embodiment, the seeding density can range from about $6.0 \times 10^3$ cells/cm$^2$ to about $1.0 \times 10^4$ cells/cm$^2$ of growth surface, such as about $6.0 \times 10^3$ cells/cm$^2$ to about $9.0 \times 10^3$ cells/cm$^2$, such as about $7.0 \times 10^3$ cells/cm$^2$ to about $1.0 \times 10^4$ cells/cm$^2$, such as about $7.0 \times 10^3$ cells/cm$^2$ to about $9.0 \times 10^3$ cells/cm$^2$, or such as about $7.0 \times 10^3$ cells/cm$^2$ to about $8.0 \times 10^3$ cells/cm$^2$ of growth surface. In yet another embodiment, the seeding density can range from about $1.0 \times 10^4$ cells/cm$^2$ to about $1.0 \times 10^5$ cells/cm$^2$ of growth surface, such as about $2.0 \times 10^4$ cells/cm$^2$ to about $9.0 \times 10^4$ cells/cm$^2$, such as about $3.0 \times 10^4$ cells/cm$^2$ to about $8.0 \times 10^4$ cells/cm$^2$, such as about $4.0 \times 10^4$ cells/cm$^2$ to about $7.0 \times 10^4$ cells/cm$^2$, or such as about $5.0 \times 10^4$ cells/cm$^2$ to about $6.0 \times 10^4$ cells/cm$^2$ of growth surface. In an embodiment, the seeding density can range from about $1.0 \times 10^5$ cells/cm$^2$ to about $5.0 \times 10^5$ cells/cm$^2$ of growth surface, such as about $1.0 \times 10^5$ cells/cm$^2$ to about $4.5 \times 10^5$ cells/cm$^2$, such as about $1.5 \times 10^5$ cells/cm$^2$ to about $4.0 \times 10^5$ cells/cm$^2$, such as about $2.0 \times 10^5$ cells/cm$^2$ to about $3.5 \times 10^5$ cells/cm$^2$, or such as about $2.5 \times 10^5$ cells/cm$^2$ to about $3.0 \times 10^5$ cells/cm$^2$ of growth surface.

Neural Induction of Undifferentiated Pluripotent Stem Cells

The present disclosure provides methods for differentiating pluripotent stem cells into neuroectoderm and further to glial progenitor cells and OPCs using small molecule and protein modulators of TGFβ/Activin/Nodal signaling and BMP signaling. Without being held to any particular theory, the inventors have discovered that starting material pluripotent stem cells can be aggregated in dynamic suspension into non-EB aggregates wherein the pluripotent stem cells remain undifferentiated and subsequently, the aggregates can be induced to differentiate into neuroectoderm while in dynamic suspension by using one or more inhibitors of TGFβ/Activin/Nodal signaling and one or more inhibitors of BMP signaling (dual SMAD inhibition). The dynamic suspension provides a scalable, reproducible and controllable process for producing large quantities of cells from the starting material, in contrast with adherent culture and EB-based methods. The methods for dual SMAD inhibition in dynamic suspension are described in detail herein.

In an embodiment, a method comprises culturing undifferentiated stem cells that have formed small non-EB aggregates but remain undifferentiated in dynamic suspension in the presence of one or more inhibitors of TGFβ/Activin/Nodal signaling and one or more inhibitors of BMP signaling, thereby commencing neural induction. In certain embodiments, the inhibitor of TGFβ/Activin/Nodal signaling is a small molecule. In other embodiments, the inhibitor of TGFβ/Activin/Nodal signaling is a protein. In some embodiments, the direct target of the inhibitor of TGFβ/Activin/Nodal signaling is ALK5, also known as TGFβ type 1 receptor (TGFBR1). In certain embodiments, the inhibitor of BMP signaling is a small molecule. In other embodiments, the inhibitor of BMP signaling is a protein. In some embodiments, the direct target of the inhibitor of BMP signaling is ALK2, also known as Activin A receptor, type I (ACVR1). In certain embodiments, subsequent to dual SMAD inhibition, the resulting cells are cultured in dynamic suspension in the presence of one or more Smoothened receptor agonists and retinoic acid.

In certain embodiments, an inhibitor of TGFβ/Activin/Nodal signaling can be selected from the group consisting of SB431542, LY2157299, GW788388, A-77-01, A-83-01 and SB505124, and derivatives thereof. In certain embodiments, an inhibitor of BMP signaling can be selected from the group consisting of Dorsomorphin, DMH-1, K02288, ML3467, LDN193189 and Noggin protein. In certain embodiments, a Smoothened agonist can be selected from the group consisting of Purmorphamine, SAG (CAS 364590-63-6), SSH protein, and derivatives thereof.

In an embodiment, a method comprises obtaining non-EB aggregates comprising pluripotent stem cells that remain in undifferentiated state; culturing the non-EB aggregates in dynamic suspension in the presence of the small molecules SB431542 and Dorsomorphin for a first time period; and subsequently culturing the aggregates in dynamic suspension in the presence of a Smoothened agonist and retinoic acid for a second time period, as depicted in FIG. 1. In an embodiment, the first time period and the second time period can each range from about 1 to about four days, such as about one day, such as about two days, such as about three days, such as about four days.

In an embodiment, a method comprises culturing non-EB aggregates in dynamic suspension in the presence of SB431542 at a concentration that ranges from about 1 µM to about 100 µM, such as about 5 µM, about 10 µM, such as about 15 µM, such as about 20 µM, such as about 25 µM, such as about 30 µM, such as about 35 µM, such as about 40 µM, such as about 45 µM, such as about 50 µM, such as about 55 µM, such as about 60 µM, such as about 65 µM, such as about 70 µM, such as about 75 µM, such as about 80 µM, such as about 85 µM, such as about 90 µM, or such as about 95 µM. In another embodiment, a method comprises culturing non-EB aggregates in dynamic suspension in the presence of SB431542 at a concentration that ranges from about 1 µM to about 20 µM, such as about 1 µM to about 13 µM, such as about 8 µM to about 20 µM, such as about 8 µM to about 13 µM, or such as about 9 µM to about 11 µM. In yet another embodiment, a method comprises culturing non-EB aggregates in dynamic suspension in the presence of SB431542 at a concentration that ranges from about 20 µM to about 40 µM, such as about 20 µM to about 33 µM, such as about 28 µM to about 40 µM, such as about 28 µM to about 33 µM, or such as about 29 µM to about 31 µM. In an embodiment, a method comprises culturing non-EB aggregates in dynamic suspension in the presence of SB431542 at a concentration that ranges from about 40 µM to about 60 µM, such as about 40 µM to about 53 µM, such as about 48 µM to about 55 µM, such as about 48 µM to about 53 µM, or such as about 49 µM to about 51 µM. In an embodiment, a method comprises culturing non-EB aggregates in dynamic suspension in the presence of SB431542 at a concentration that ranges from about 60 µM to about 80 µM, such as about 60 µM to about 73 µM, such as about 68 µM to about 75 µM, such as about 68 µM to about 73 µM, or such as about 69 µM to about 71 µM. In an embodiment, a method comprises culturing non-EB aggregates in dynamic suspension in the presence of SB431542 at a concentration that ranges from about 80 µM to about 100 µM, such as about 80 µM to about 93 µM, such as about 88 µM to about 95 µM, such as about 88 µM to about 93 µM, or such as about 89 µM to about 91 µM. In an embodiment, a method comprises culturing non-EB aggregates in dynamic suspension in the presence of SB431542 at a concentration of about 10 µM.

In an embodiment, a method comprises culturing non-EB aggregates in dynamic suspension in the presence of an ALK5 inhibitor at a concentration that ranges from about 250 nM to about 250 µM, such as about 1 µM, about 10 µM, about 50 µM, about 100 µM, about 150 µM, or about 200 µM. In an embodiment, a method comprises culturing non-EB aggregates in dynamic suspension in the presence of an ALK5 inhibitor at about 10 µM.

In an embodiment, a method comprises culturing non-EB aggregates in dynamic suspension in the presence of an LY364947 at a concentration that ranges from about 250 nM to about 250 µM, such as about 1 µM, about 10 µM, about 50 µM, about 100 µM, about 150 µM, or about 200 µM. In an embodiment, a method comprises culturing non-EB aggregates in dynamic suspension in the presence of LY364947 at about 10 µM.

In an embodiment, a method comprises culturing non-EB aggregates in dynamic suspension in the presence of GW788388 at a concentration that ranges from about 250 nM to about 250 µM, such as about 1 µM, about 10 µM, about 50 µM, about 100 µM, about 150 µM, or about 200 µM. In an embodiment, a method comprises culturing non-EB aggregates in dynamic suspension in the presence of GW788388 at about 10 µM.

In an embodiment, a method comprises culturing non-EB aggregates in dynamic suspension in the presence of A-77-01 at a concentration that ranges from about 250 nM to about 250 µM, such as about 1 µM, about 10 µM, about 50 µM, about 100 µM, about 150 µM, or about 200 µM. In an embodiment, a method comprises culturing non-EB aggregates in dynamic suspension in the presence of A-77-01 at about 10 µM.

In an embodiment, a method comprises culturing non-EB aggregates in dynamic suspension in the presence of A-83-01 at a concentration that ranges from about 250 nM to about 250 µM, such as about 1 µM, about 10 µM, about 50 µM, about 100 µM, about 150 µM, or about 200 µM. In an embodiment, a method comprises culturing non-EB aggregates in dynamic suspension in the presence of A-83-01 at about 10 µM.

In an embodiment, a method comprises culturing non-EB aggregates in dynamic suspension in the presence of SB505124 at a concentration that ranges from about 250 nM to about 250 µM, such as about 1 µM, about 10 µM, about 50 µM, about 100 µM, about 150 µM, or about 200 µM. In an embodiment, a method comprises culturing non-EB aggregates in dynamic suspension in the presence of SB505124 about 10 µM.

In an embodiment, a method comprises culturing non-EB aggregates in dynamic suspension in the presence of Dorsomorphin at a concentration that ranges from about 0.2 µM to about 20 µM, such as about 0.5 µM, such as about 0.8 µM, such as about 1 µM, such as about 1.5 µM, such as about 2 µM, such as about 2.5 µM, such as about 3 µM, such as about 3.5 µM, such as about 4 µM, such as about 4.5 µM, such as about 5 µM, such as about 5.5 µM, such as about 6 µM, such as about 6.5 µM, such as about 7 µM, such as about 7.5 µM, such as about 8 µM, such as about 8.5 µM, such as about 9 µM, such as about 10 µM, such as about 11 µM, such as about 12 µM, such as about 13 µM, such as about 14 µM, such as about 15 µM, such as about 16 µM, such as about 17 µM, such as about 18 µM, or such as about 19 µM. In another embodiment, a method comprises culturing non-EB aggregates in dynamic suspension in the presence of Dorsomorphin at a concentration that ranges from about 0.2 µM to about 1 µM, such as about 0.2 µM to about 0.9 µM, such as about 0.3 µM to about 0.8 µM, such as about 0.4 µM to about 0.7 µM, or such as about 0.5 µM to about 0.6 µM. In yet another embodiment, a method comprises culturing non-EB aggregates in dynamic suspension in the presence of Dorsomorphin at a concentration that ranges from about 1 µM to about 10 such as about 1 µM to about 9 such as about 2 µM to about 8 such as about 3 µM to about 7 or such as about 4 µM to about 6 µM. In an embodiment, a method comprises culturing non-EB aggregates in dynamic suspension in the presence of Dorsomorphin at a concentration that ranges from about 10 µM to about 20 such as about 10 µM to about 19 such as about 12 µM to about 18 such as about 13 µM to about 17 or such as about 14 µM to about 16 µM. In an embodiment, a method comprises culturing non-EB aggregates in dynamic suspension in the presence of Dorsomorphin at a concentration of about 2 µM.

In an embodiment, a method comprises culturing non-EB aggregates in dynamic suspension in the presence of an ALK2 inhibitor at a concentration that ranges from about 1 nM to about 20 such as about 10 nM, about 50 nM, about 100 nM, about 150 nM, about 200 nM, about 500 nM, about 1 about 5 about 10 or about 15 µM.

In an embodiment, a method comprises culturing non-EB aggregates in dynamic suspension in the presence of DMH-1 at a concentration that ranges from about 1 µM to about 10 µM. In an embodiment, a method comprises culturing non-EB aggregates in dynamic suspension in the presence of DMH-1 at about 2 µM.

In an embodiment, a method comprises culturing non-EB aggregates in dynamic suspension in the presence of K02288 at a concentration that ranges from about 1 µM to about 10 µM. In an embodiment, a method comprises culturing non-EB aggregates in dynamic suspension in the presence of K02288 at about 2 µM.

In an embodiment, a method comprises culturing non-EB aggregates in dynamic suspension in the presence of ML347 at a concentration that ranges from about 1 µM to about 10 µM. In an embodiment, a method comprises culturing non-EB aggregates in dynamic suspension in the presence of ML347 at about 2 µM.

In an embodiment, a method comprises culturing non-EB aggregates in dynamic suspension in the presence of Purmorphamine at a concentration that ranges from about 0.05 µM to about 5 such as about 0.08 such as about 0.1 such as about 0.2 such as about 0.3 such as about 0.4 such as about 0.5 such as about 0.6 such as about 0.7 such as about 0.8 such as about 0.9 such as about 1 such as about 2 such as about 3 such as about 4 µM. In another embodiment, a method comprises culturing non-EB aggregates in dynamic suspension in the presence of Purmorphamine at a concentration that ranges from about 0.05 µM to about 0.1 such as about 0.06 µM to about 0.09 or such as about 0.07 µM to about 0.08 µM. In another embodiment, a method comprises culturing non-EB aggregates in dynamic suspension in the presence of Purmorphamine at a concentration that ranges from about 0.1 µM to about 1 such as about 0.2 µM to about 0.9 such as about 0.3 µM to about 0.8 such as about 0.4 µM to about 0.7 or such as about 0.5 µM to about 0.6 µM. In another embodiment, a method comprises culturing non-EB aggregates in dynamic suspension in the presence of Purmorphamine at a concentration that ranges from about 1 µM to about 5 such as about 1 µM to about 4 such as about 2 µM to about 5 or such as about 2 µM to about 4 µM. In an embodiment, a method comprises incubating expanded but undifferentiated ESCs with Purmorphamine at a concentration of about 0.5 µM.

In an embodiment, a method comprises culturing non-EB aggregates in dynamic suspension in the presence of a Smoothened agonist at a concentration that ranges from about 2.5 nM to about 5 such as about 50 nM, about 100 nM, about 250 nM, about 500 nM, about 750 nM, about 1 or about 2.5 µM.

In an embodiment, a method comprises incubating culturing non-EB aggregates in dynamic suspension in the presence of SAG at a concentration that ranges from about 10 nM to about 1 such as about 10 nM to about 100 nM, such as about 100 nM to about 500 nM, or such as about 500 nM to about 1000 nM. In an embodiment, a method comprises culturing non-EB aggregates in dynamic suspension in the presence of SAG at about 0.5 µM.

In an embodiment, a method comprises culturing non-EB aggregates in dynamic suspension in the presence of SHH protein at a concentration that ranges from about 2.5 nM to about 250 nM, such as about 2.5 nM to about 10 nM, such as about 10 nM to about 100 nM, or such as about 100 nM to about 250 nM. In an embodiment, a method comprises culturing non-EB aggregates in dynamic suspension in the presence of SHH protein at about 25 nM.

Any cell culture vessels or reactors suitable for dynamic suspension culture can be used for the differentiation steps contemplated in the present disclosure. The vessel walls are typically inert or resistant to adherence of the cultured cells. There is also a means for preventing the cells from settling out, such as a stirring mechanism like a magnetically or mechanically driven stir bar or paddle, a shaking mechanism (typically attached to the vessel by the outside), or an inverting mechanism (i.e., a device that rotates the vessel so as to change the direction of gravity upon the cells).

Vessels suitable for suspension culture for process development include the usual range of commercially available spinner, rocker bag, or shaker flasks. Exemplary bioreactors suitable for commercial production include the Vertical-Wheel™ Bioreactors (PBS Biotech, Camarillo, CA).

OPC Compositions

The methods of the present disclosure can be used to obtain compositions comprising oligodendrocyte progenitor cells (OPCs) that are suitable for cellular therapy. The OPCs obtained according to the present disclosure express a high level of the proteoglycan NG2 characteristics of OPCs and low levels of non-OPC markers associated with undesirable cell types, such as CD49f, which can be expressed by both neural progenitor cells and epithelial cells and is associated with in vitro cyst formation (Debnath J, Muthuswamy S K, Brugge J S. Morphogenesis and oncogenesis of MCF-10A mammary epithelial acini grown in three-dimensional basement membrane cultures. 2003 Methods. 3:256-68), or CLDN6 and EpCAM, two markers expressed by both pluripotent cells and epithelial cells (Lin D, Guo Y, Li Y, Ruan Y, Zhang M, Jin X, Yang M, Lu Y, Song P, Zhao S, Dong B, Xie Y, Dang Q, Quan C. Bioinformatic analysis reveals potential properties of human Claudin-6 regulation and functions. *Oncol Rep.* 2017 August; 38 (2):875-885; Huang L, Yang Y, Yang F, Liu S, Zhu Z, Lei Z, Guo J. Functions of EpCAM in physiological processes and diseases (Review). *Int J. Mol Med.* 2018 October; 42 (4): 1771-1785).

In certain embodiments, the OPCs generated in accordance of the present disclosure are the in vitro differentiated progeny of human pluripotent stem cells. In certain embodiments, the OPCs obtained in accordance of the present disclosure are the in vitro differentiated progeny of human embryonic stem cells. In other embodiments, the OPCs obtained in accordance of the present disclosure are the in vitro differentiated progeny of induced pluripotent stem (iPS) cells.

One or more characteristics of the OPC population obtained can be determined by quantifying various cell markers using flow cytometry, for example, to determine what percentage of the cell population is positive for a particular marker or set of markers or to identify undesirable cell types present in the OPC population. In one embodiment, the OPCs prepared according to the methods of the invention express one or more of the markers selected from NG2, PDGFRα and GD3.

An OPC population obtained according to the present disclosure can comprise from about 30% to about 100% NG2 positive cells, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 98%, such as at least about 99%, such as at least about 99.5%, such as at least about 99.8%, or such as at least about 99.9% NG2 positive cells. In certain embodiments, an OPC population obtained according to the present disclosure can comprise from about 45% to about 75% NG2 positive cells, such as about 45% to about 50%, such as about 50% to about 55%, such as about 55% to about 60%, such as about 60% to about 65%, such as about 65% to about 70%, such as about 70% to about 75%, such as about 50% to about 70%, such as about 55% to about 65%, or such as about 58% to about 63% NG2 positive cells. In other embodiments, an OPC population obtained according to the present disclosure can comprise from about 60% to about 90% NG2 positive cells, such as about 60% to about 65%, such as about 65% to about 70% positive cells. An OPC population obtained according to the present disclosure can comprise from about 30% to about 100% PDGFRα positive cells, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 98%, such as at least about 99%, such as at least about 99.5%, such as at least about 99.8%, or such as at least about 99.9% PDGFRα positive cells. In certain embodiments, an OPC population obtained according to the present disclosure can comprise from about 45% to about 75% PDGFRα positive cells, such as about 45% to about 50%, such as about 50% to about 55%, such as about 55% to about 60%, such as about 60% to about 65%, such as about 65% to about 70%, such as about 70% to about 75%, such as about 50% to about 70%, such as about 55% to about 65%, or such as about 58% to about 63% PDGFRα positive cells. In other embodiments, an OPC population obtained according to the present disclosure can comprise from about 60% to about 90% PDGFRα positive cells, such as about 60% to about 65%, such as about 65% to about 70% positive cells. An OPC population obtained according to the present disclosure can comprise from about 30% to about 100% GD3 positive cells, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 98%, such as at least about 99%, such as at least about 99.5%, such as at least about 99.8%, or such as at least about 99.9% GD3 positive cells. In certain embodiments, an OPC population obtained according to the present disclosure can comprise from about 45% to about 75% GD3 positive cells, such as about 45% to about 50%, such as about 50% to about 55%, such as about 55% to about 60%, such as about 60% to about 65%, such as about 65% to about 70%, such as about 70% to about 75%, such as about 50% to about 70%, such as about 55% to about 65%, or such as about 58% to about 63% GD3 positive cells. In other embodiments, an OPC population obtained according to the present disclosure can comprise from about 60% to about 90% GD3 positive cells, such as about 60% to about 65%, such as about 65% to about 70% positive cells.

In an embodiment, an OPC population obtained according to the present disclosure can be capable of forming less than or equal to four epithelial cysts per 100,000 cells in a cyst assay as described in Example 8 of the present disclosure. In another embodiment, an OPC population obtained according to the present disclosure can be capable of forming less than or equal to three epithelial cysts per 100,000 cells in a cyst assay. In another embodiment, OPC population obtained according to the present disclosure can be capable of forming less than or equal to two epithelial cysts per 100,000 cells in a cyst assay. In yet another embodiment, an OPC population obtained according to the present disclosure can be capable of forming less than or equal to one epithelial cysts per 100,000 cells in a cyst assay as described in Example 8 of the present disclosure.

Undesirable Cell Types

OPC populations obtained according to the present disclosure contain low levels of undesired ell types, as measured, for example, by quantification of markers associated with undesirable cell types by flow cytometry. In a non-limiting example, the Day 42 OPCs obtained according to the present disclosure contained between 0% to 4% of cells expressing the epithelial cell associated markers EpCAM, CD49f, and CLDN6 (Example 5, Table 2).

Markers associated with undesirable cell types can comprise less than about 20% undesirable cell types, such as less than about 19%, such as less than about 18%, such as less than about 17%, such as less than about 16%, such as less than about 15%, such as less than about 14%, such as less than about 13%, such as less than about 12%, such as less than about 11%, such as less than about 10%, such as less than about 9%, such as less than about 8%, such as less than about 7%, such as less than about 6%, such as less than about 5%, such as less than about 4%, such as less than about 3%, such as less than about 2%, such as less than about 1%, such as less than about 0.5%, such as less than about 0.1%, such as less than about 0.05%, or such as less than about 0.01% undesirable cell types. In another embodiment, a cell population can comprise from about 15% to about 20% undesirable cell types, such as about 19% to about 20%, such as about 18% to about 20%, such as about 17% to about 20%, such as about 16% to about 20%, such as about 15% to about 19%, or such as about 16% to about 18% undesirable cell types. In yet another embodiment, a cell population can comprise from about 10% to about 15% undesirable cell types, such as about 14% to about 15%, such as about 13% to about 15%, such as about 12% to about 15%, such as about 11% to about 15%, or such as about 12% to about 14% undesirable cell types. In an embodiment, a cell population can comprise from about 1% to about 10% undesirable cell types, such as about 2% to about 10%, such as about 1% to about 9%, such as about 2% to about 8%, such as about 3% to about 7%, or such as about 4% to about 6% undesirable cell types. In an embodiment, a cell population can comprise from about 0.1% to about 1% undesirable cell types, such as about 0.2% to about 1%, such as about 0.1% to about 0.9%, such as about 0.2% to about 0.8%, such as about 0.3% to about 0.7%, or such as about 0.4% to about 0.6% undesirable cell types. In an embodiment, a cell population can comprise from about 0.01% to about 0.1% undesirable cell types, such as about 0.02% to about 0.1%, such as about 0.01% to about 0.09%, such as about 0.02% to about 0.08%, such as about 0.03% to about 0.07%, or such as about 0.04% to about 0.06% undesirable cell types. In an embodiment, low levels of undesirable cell types can denote the presence of less than about 15% undesirable cell types.

In an embodiment, an undesirable cell type can comprise cells expressing one more markers selected from CD49f, CLDN6, or EpCAM.

Formulation

OPC compositions in accordance with the present disclosure can further comprise a pharmaceutically-acceptable carrier. In an embodiment, a pharmaceutically-acceptable carrier can comprise dimethyl sulfoxide (DMSO). In an embodiment, a pharmaceutically-acceptable carrier does not comprise dimethyl sulfoxide. In an embodiment, a composition can be adapted for cryopreservation at or below −80° C. to −195° C.

OPC compositions in accordance with the present disclosure can be formulated for administration via a direct injection to the spinal cord of a subject. In an embodiment, an OPC composition in accordance with the present disclosure can be formulated for intracerebral, intraventricular, intrathecal, intranasal, or intracisternal administration to a subject. In an embodiment, an OPC composition in accordance with the present disclosure can be formulated for administration via an injection directly into or immediately adjacent to an infarct cavity in the brain of a subject. In an embodiment, a composition in accordance with the present disclosure can be formulated for administration through implantation. In an embodiment, a composition in accordance with the present disclosure can be formulated as a solution.

An OPC composition in accordance with the present disclosure can comprise from about $1 \times 10^6$ to about $5 \times 10^8$ cells per milliliter, such as about $1 \times 10^6$ cells per milliliter, such as about $2 \times 10^6$ cells per milliliter, such as about $3 \times 10^6$ cells per milliliter, such as about $4 \times 10^6$ cells per milliliter, such as about $5 \times 10^6$ cells per milliliter, such as about $6 \times 10^6$ cells per milliliter, such as about $7 \times 10^6$ cells per milliliter, such as about $8 \times 10^6$ cells per milliliter, such as about $9 \times 10^6$ cells per milliliter, such as about $1 \times 10^7$ cells per milliliter, such as about $2 \times 10^7$ cells per milliliter, such as about $3 \times 10^7$ cells per milliliter, such as about $4 \times 10^7$ cells per milliliter, such as about $5 \times 10^7$ cells per milliliter, such as about $6 \times 10^7$ cells per milliliter, such as about $7 \times 10^7$ cells per milliliter, such as about $8 \times 10^7$ cells per milliliter, such as about $9 \times 10^7$ cells per milliliter, such as about $1 \times 10^8$ cells per milliliter, such as about $2 \times 10^8$ cells per milliliter, such as about $3 \times 10^8$ cells per milliliter, such as about $4 \times 10^8$ cells per milliliter, or such as about $5 \times 10^8$ cells per milliliter. In another embodiment, a composition in accordance with the present disclosure can comprise from about $1 \times 10^8$ to about $5 \times 10^8$ cells per milliliter, such as about $1 \times 10^8$ to about $4 \times 10^8$ cells per milliliter, such as about $2 \times 10^8$ to about $5 \times 10^8$ cells per milliliter, such as about $1 \times 10^8$ to about $3 \times 10^8$ cells per milliliter, such as about $2 \times 10^8$ to about $4 \times 10^8$ cells per milliliter, or such as about $3 \times 10^8$ to about $5 \times 10^8$ cells per milliliter. In yet another embodiment, a composition in accordance with the present disclosure can comprise from about $1 \times 10^7$ to about $1 \times 10^8$ cells per milliliter, such as about $2 \times 10^7$ to about $9 \times 10^7$ cells per milliliter, such as about $3 \times 10^7$ to about $8 \times 10^7$ cells per milliliter, such as about $4 \times 10^7$ to about $7 \times 10^7$ cells per milliliter, or such as about $5 \times 10^7$ to about $6 \times 10^7$ cells per milliliter. In an embodiment, a composition in accordance with the present disclosure can comprise from about $1 \times 10^6$ to about $1 \times 10^7$ cells per milliliter, such as about $2 \times 10^6$ to about $9 \times 10^6$ cells per milliliter, such as about $3 \times 10^6$ to about $8 \times 10^6$ cells per milliliter, such as about $4 \times 10^6$ to about $7 \times 10^6$ cells per milliliter, or such as about $5 \times 10^6$ to about $6 \times 10^6$ cells per milliliter. In yet another embodiment, a composition in accordance with the present disclosure can comprise at least about $1 \times 10^6$ cells per milliliter, such as at least about $2 \times 10^6$ cells per milliliter, such as at least about $3 \times 10^6$ cells per milliliter, such as at least about $4 \times 10^6$ cells per milliliter, such as at least about $5 \times 10^6$ cells per milliliter, such as at least about $6 \times 10^6$ cells per milliliter, such as at least about $7 \times 10^6$ cells per milliliter, such as at least about $8 \times 10^6$ cells per milliliter, such as at least about $9 \times 10^6$ cells per milliliter, such as at least about $1 \times 10^7$ cells per milliliter, such as at least about $2 \times 10^7$ cells per milliliter, such as at least about $3 \times 10^7$ cells per milliliter, such as at least about $4 \times 10^7$ cells per milliliter, or such as at least about $5 \times 10^7$ cells per milliliter. In an embodiment, a composition in accordance with the present disclosure can comprise up to about $1 \times 10^8$ cells or more, such as up to about $2 \times 10^8$ cells per milliliter or more, such as up to about $3 \times 10^8$ cells per milliliter or more, such as up to about $4 \times 10^8$ cells per milliliter or more, such as up to about $5 \times 10^8$ cells per milliliter or more, or such as up to about $6 \times 10^8$ cells per milliliter.

In an embodiment, an OPC composition in accordance with the present disclosure can comprise from about $4 \times 10^7$ to about $2 \times 10^8$ cells per milliliter.

In yet another embodiment, an OPC composition in accordance with the present disclosure can have a volume ranging from about 10 microliters to about 5 milliliters, such as about 20 microliters, such as about 30 microliters, such as about 40 microliters, such as about 50 microliters, such as about 60 microliters, such as about 70 microliters, such as about 80 microliters, such as about 90 microliters, such as about 100 microliters, such as about 200 microliters, such as about 300 microliters, such as about 400 microliters, such as about 500 microliters, such as about 600 microliters, such as about 700 microliters, such as about 800 microliters, such as about 900 microliters, such as about 1 milliliter, such as about 1.5 milliliters, such as about 2 milliliters, such as about 2.5 milliliters, such as about 3 milliliters, such as about 3.5 milliliters, such as about 4 milliliters, or such as about 4.5 milliliters. In an embodiment, a composition in accordance with the present disclosure can have a volume ranging from about 10 microliters to about 100 microliters, such as about 20 microliters to about 90 microliters, such as about 30 microliters to about 80 microliters, such as about 40 microliters to about 70 microliters, or such as about 50 microliters to about 60 microliters. In another embodiment, a composition in accordance with the present disclosure can have a volume ranging from about 100 microliters to about 1 milliliter, such as about 200 microliters to about 900 microliters, such as about 300 microliters to about 800 microliters, such as about 400 microliters to about 700 microliters, or such as about 500 microliters to about 600 microliters. In yet another embodiment, a composition in accordance with the present disclosure can have a volume ranging from about 1 milliliter to about 5 milliliters, such as about 2 milliliter to about 5 milliliters, such as about 1 milliliter to about 4 milliliters, such as about 1 milliliter to about 3 milliliters, such as about 2 milliliter to about 4 milliliters, or such as about 3 milliliter to about 5 milliliters. In an embodiment, an OPC composition in accordance with the present disclosure can have a volume of about 20 microliters to about 500 microliters. In another embodiment, an OPC composition in accordance with the present disclosure can have a volume of about 50 microliters to about 100 microliters. In yet another embodiment, an OPC composition in accordance with the present disclosure can have a volume of about 50 microliters to about 200 microliters. In another embodiment, an OPC composition in accordance with the present disclosure can have a volume of about 20 microliters to about 400 microliters. In an embodiment, an OPC composition in accordance with the present disclosure can be in a container configured for cryopreservation or for administration to a subject in need thereof. In an embodiment, a container can be a prefilled syringe.

Methods of Use

An OPC composition obtained in accordance with the present disclosure can be used in cellular therapy to improve one or more neurological functions in a subject in need of treatment. In an embodiment, an OPC cell population in accordance with the present disclosure can be injected or implanted into a subject in need thereof. In an embodiment, a cell population in accordance with the present disclosure can be implanted into a subject in need thereof for treating spinal cord injury, stroke, or multiple sclerosis.

In an embodiment, a cell population in accordance with the present disclosure can be capable of inducing myelination of denuded axons at an implantation site in a subject. In an embodiment, a cell population generated in accordance with a method of the present disclosure can exhibit improved capacity for engraftment and migration. In an embodiment, a cell population generated in accordance with a method of the present disclosure can be capable of improving post-injury repair or regeneration of neural tissue in a subject.

A cell population in accordance with the present disclosure can be capable of improving a sensory function in a subject in need of therapy following implantation of the population into the subject. Improvements in a sensory function can be evaluated using the International Standards for Neurological Classification of Spinal Cord Injury (ISNCSCI) Exam, such as determining sensory levels for right and left sides for pin prick and light touch sensations. A cell population in accordance with the present disclosure can be capable of improving a motor function in a subject in need of therapy following implantation of the population into the subject. An improved motor function can be evaluated using the ISNCSCI Exam, such as determining motor levels for right and left sides for total paralysis, palpable or visible contraction, active movement, full range of motion against gravity, and sufficient resistance.

A cell population in accordance with the present disclosure can be capable of reducing a volume of an injury-induced central nervous system parenchymal cavitation in 12 months or less. In an embodiment, a cell population in accordance with the present disclosure can be capable of reducing a volume of an injury-induced central nervous system parenchymal cavitation in a subject in 6 months or less, 5 months or less, 4 months or less, 3 months or less, 2 months or less, or less than 1 month.

Having now generally described the invention, the same will be more readily understood through reference to the following examples that are provided by way of illustration, and are not intended to be limiting of the present disclosure, unless specified.

EXAMPLES

Example 1—Culture and Expansion of Undifferentiated Human Embryonic Stem Cells Undifferentiated human embryonic stem cells (uhFSC) from a working cell bank (WCB) generated from the H1 line (WA01; Thomson J A, Itskovitz-Eldor J, Shapiro S S, Waknitz M A, Swiergiel J J, Marshall V S, Jones J M. Embryonic stem cell lines derived from human blastocysts. *Science.* 1998 Nov. 6; 282 (5391):1145-7) were cultured on recombinant human laminin-521 (Corning #354224) coated, tissue culture treated polystyrene 225 cm$^2$ culture flasks (Corning #431082) in complete mTeSlem-1 medium (Stem Cell Technologies #85850). The medium was completely exchanged daily until the cells reached approximately 80-90% confluency, and uhFSCs were then passaged using ReLeSR™ reagent (Stem Cell Technologies #05872). ReLeSR™-lifted uhFSC cells were seeded in new laminin-521 coated 225 cm$^2$ flasks, and daily medium exchange was resumed two days post-seeding. Cultured uhFSCs from the WCB were expanded in this manner for between two to five passages, depending on the experiment, prior to differentiation into neuroectoderm progenitor cells as described in Example 2.

Figure 5:
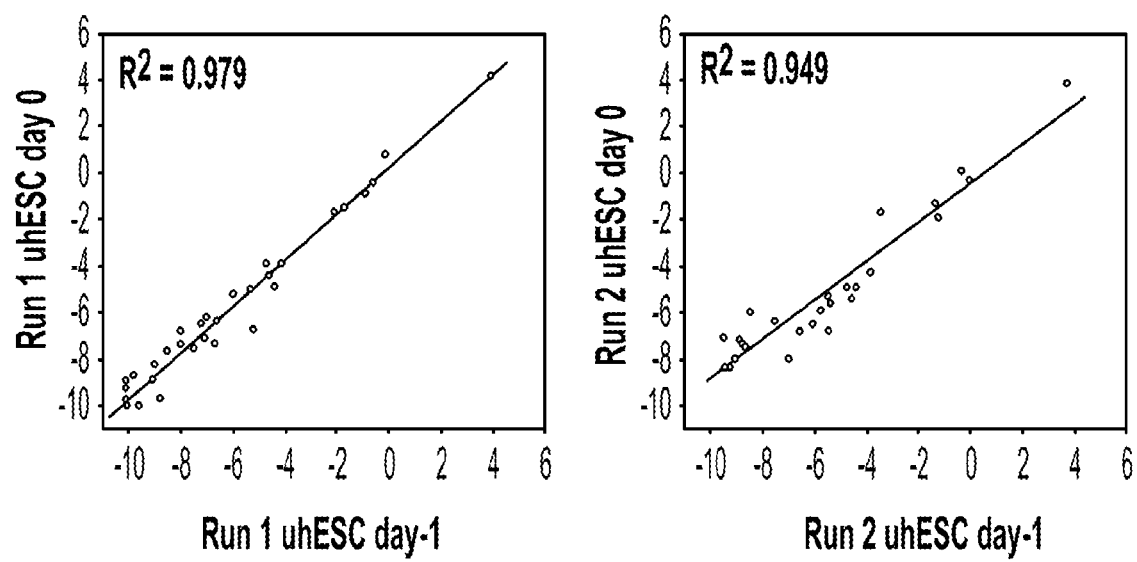
FIG. 5 shows correlation plots of the gene expression profile of uhFSCs before and 24 hours after formation of cellular aggregates in suspension. Each correlation plot shows a comparison of the gene expression profile for Day −1 (before aggregate formation) versus Day 0 (24 hours after aggregate formation) from two separate experiments. For each plot, the data points represent each of the 76 genes assessed by Fluidigm qPCR and calculated as the normalized ΔCT as described in Example 6. R-squared values are shown in the upper left corner of each plot and were calculated based on the best-fit line using JMP software (SAS, Cary, NC, USA).

Example 2—Method of Differentiating Human Embryonic Stem Cells to Neuroectoderm Progenitors in Dynamic Suspension Culture Day −1: Expanded iihFSC (at approximately 90% confluency) were detached and disaggregated with Accutase® (Stem Cell Technologies #07920) to form a single-cell suspension, allowing for an accurate cell count and uniform seeding densities. The disaggregated uhFSC were then seeded for dynamic suspension culture at a concentration of 1×10$^6$ viable cells/mL, into PBS-0.1 or PBS-0.5 Mini Bioreactor System (PBS Biotech), set to rotate at 35 RPM or 25 RPM, respectively (Day −1). Cells were seeded in a 1:1 mixture of glial progenitor medium (GPM; consisting of DMEM/F12 (Gibco Catalog No. 10565-018) supplemented with 2% B27 supplement (Gibco Catalog No. 17504-044), and 0.04 μg/mL tri-iodo-thyronine (Sigma Catalog No. T5516-1MG)) and undifferentiated hESC culture medium (as in Example 1), supplemented with 10 μM Rho Kinase Inhibitor (RI, Tocris Catalog No. 1254) to support cell survival. Within the first 24 hours, small, uniform aggregates of lihFSC formed. In contrast with embryoid body (EB) formation, the cells in the small aggregates did not begin to spontaneously differentiate but maintained their pluripotency, as demonstrated by marker expression as measured by qPCR (FIG. 5).

Days 0-3: To initiate differentiation to neuroectoderm, the small, non-EB aggregates were cultured in dynamic suspension in the PBS-0.1 or PBS-0.5 Mini Bioreactors rotating at 45 or 32 RPM, respectively, for the next four days in GPM supplemented with 10 μM SB431542 (Sigma-Aldrich, Catalog No. 54317) and 2 μM Dorsomorphin (Sigma-Aldrich, Catalog No. P5499). The medium was replenished daily by allowing the aggregates to settle, removing 70-80% of the spent medium, and replacing with an equal volume of GPM supplemented with 10 μM SB431542 and 2 μM Dorsomorphin.

Days 4-6: The cells were further cultured in dynamic suspension for an additional three days at 45 RPM (PBS-0.1 Mini Bioreactor) or 32 RPM (PBS-0.5 Mini Bioreactor) in GPM supplemented with 0.5 μM Purmorphamine (Reprocell, Catalog No. 04-0009), 1 μM retinoic acid (Sigma-Aldrich, Catalog No. R2625), and 150 μM ascorbic acid (Sigma Aldrich, Catalog No. A4544). The medium was replenished daily by allowing the aggregates to settle, removing 70-80% of the spent medium, and replacing with an equal volume of GPM supplemented with 0.5 μM Purmorphamine, 1 μM retinoic acid, and 150 μM ascorbic acid.

Day 7: A subset of the differentiated cells were collected at Day 7 of the dynamic suspension culture differentiation process and subjected to analysis for marker expression by immunocytochemistry (ICC) (as described in Example 5) and qPCR (as described in Example 6). By Day 7, the cells expressed markers characteristic of neuroectoderm (TABLE 2, FIG. 3). The remaining Day 7 cells were subjected to differentiation to glial lineage cells and further to oligodendrocyte progenitor cells, as described in Examples 3 and 4, respectively.

Example 3—Method of Differentiating Human Embryonic Stem Cells to Glial Lineage Cells in Dynamic Suspension Culture Differentiation of iihFSC to neuroectoderm/neural progenitor cells (Days 0-6) was performed as described in Example 2. On Day 7, differentiation to glial progenitor cells was initiated by modifying the differentiation medium to GPM supplemented with 20 ng/mL human basic fibroblast growth factor (hbFGF, Thermo Fisher, cat #PHG0263), 10 ng/mL epidermal growth factor (EGF, Thermo Fisher, cat #PHG0311), and 10 μM RI. Cellular aggregates were maintained in dynamic suspension at 45 rpm (PBS-0.1 Mini Bioreactor) or 32 RPM (PBS-0.5 Mini Bioreactor) in GPM supplemented with 20 ng/mL bFGF and 10 ng/mL EGF for the next two weeks (Days 8-20), with medium replenished daily using gravity sedimentation and 70-80% medium exchange. 10 μM RI was also added to the fresh medium on Day 14.

A subset of the differentiated cells were collected at Day 21 of the dynamic suspension culture differentiation process and subjected to analysis for marker expression by qPCR (as described in Example 6). By Day 21, the differentiated cells expressed markers consistent with glial lineage cells (TABLE 2).

Example 4—Method of Differentiating Human Embryonic Stem Cells to Oligodendrocyte Progenitor Cells The glial lineage precursor cells obtained in Example 3 were further differentiated into oligodendrocyte progenitor cells. The differentiation protocol for Days 0-20 was as described in Examples 2 and 3. On Day 21, the aggregates were transferred from dynamic suspension culture to adherent culture on tissue culture vessels coated with recombinant human laminin-521 (rhLN-521). For example, starting with 1×PBS-0.1 L Mini Bioreactor with 60 mL of aggregate suspension, the 60 mL of culture was split onto 2×T75 flasks, each with 30 mL of culture. Commencing on Day 21 and continuing through the end of the differentiation process, the cells were cultured in GPM supplemented with 20 ng/mL EGF and 10 ng/mL platelet-derived growth factor-AA (PDGF-AA, PeproTech, cat #AF-100-13A), with a full medium replacement performed on every other day. On Days 28 and 35, the cell cultures were detached using TrypLE™ Select (Thermo Fisher, cat #A12859-01), counted and seeded onto rhLN-521-coated vessels at 4×104 viable cells/cm². The GPM was replaced on alternating days starting on Day 35 until harvest on Day 42.

A subset of the differentiated cells were collected at Day 42 of the differentiation process and subjected to analysis for marker expression by flow cytometry (as described in Example 5), immunocytochemistry (as described in Example 5) and qPCR (as described in Example 6). By Day 42, the differentiated cells expressed markers characteristic of oligodendrocyte progenitor cells as measured by the three analytical methods (TABLE 1, TABLE 2, FIG. 4).

The OPCs were harvested on Day 42. Cells were detached from vessels using TrypLE™ Select, counted, and re-formulated in CryoStor10 (BioLife Solutions, cat #210102) prior to cryopreservation.

Example 5—Characterization of Differentiated Cell Populations by Immunocytochemistry and Flow Cytometry Flow cytometry and immunocytochemistry (ICC) can be used to detect and characterize different aspects of protein marker expression in a cell population. While flow cytometry can be used to quantify the percentage of individual cells within the population that exhibit a given protein marker profile, ICC provides additional information about the subcellular localization of each protein marker and can be applied to single cells or cellular aggregates. By using either or both of these protein profiling approaches, we tracked the differentiation of human embryonic stem cells to neuroectoderm progenitor cells, glial progenitor cells, and oligodendrocyte progenitor cells according to the methods of the present disclosure.

For human embryonic stem cells differentiated into neuroectoderm progenitor cells in suspension, protein marker expression in the starting material (undifferentiated pluripotent cells) and in the differentiated Day 7 cellular aggregates was characterized by ICC. Adherent pluripotent cells and cellular aggregates were fixed in 4% paraformaldehyde (PFA) for 30 minutes at room temperature (RT). Fixed cells and aggregates were washed with phosphate buffered saline (PBS), and fixed aggregates were then sequentially placed in increasing concentrations of sucrose solution (10%, 20%, and 30% weight/volume) for 30 minutes at RT, 30 minutes at RT, and overnight at 4° C., respectively. Following sucrose replacement, aggregates were embedded in Tissue-Tek Optimal Cutting Temperature (OCT) solution (Sakura Finetek USA #4583) and frozen at −80° C. OCT-embedded aggregates were warmed to −20° C., cut into 30 μm sections using a cryostat (model CM3050 S, Leica Biosystems, Buffalo Grove, IL, USA), and mounted onto poly-L-lysine (Sigma-Aldrich #P4707) coated glass slides. To perform immunocytochemical staining, fixed adherent cells and slide-mounted aggregate sections were permeabilized and blocked in blocking solution consisting of 0.1% Triton™ X-100/2% normal goat serum/1% bovine serum albumin in PBS for 2 hours at room temperature (RT). Following permeabilization and blocking, adherent cells and aggregate sections were incubated overnight at 4° C. in blocking solution without Triton™ X-100 and containing primary antibodies specific to protein markers of interest, including Nanog (Abcam #ab21624), Oct4 (Millipore #MAB4401), and Sox2 (Abcam #ab92494) to detect pluripotent cells, or PAX6 (BD Pharmingen #561462) and PSA-NCAM (Invitrogen #14-9118-80) to detect neuroectoderm progenitor cells. Adherent cells and aggregate sections were then washed three times with PBS followed by incubation with secondary antibodies specific to the chosen primary antibodies and 4',6-diamidino-2-phenylindole (DAPI) counterstain in blocking solution without Triton™ X-100 for 1 hour at RT protected from light. Adherent cells and aggregate sections were washed three times with PBS and imaged using an IN Cell Analyzer 2000 (GE Healthcare, Pittsburgh, PA, USA).

Figure 2:
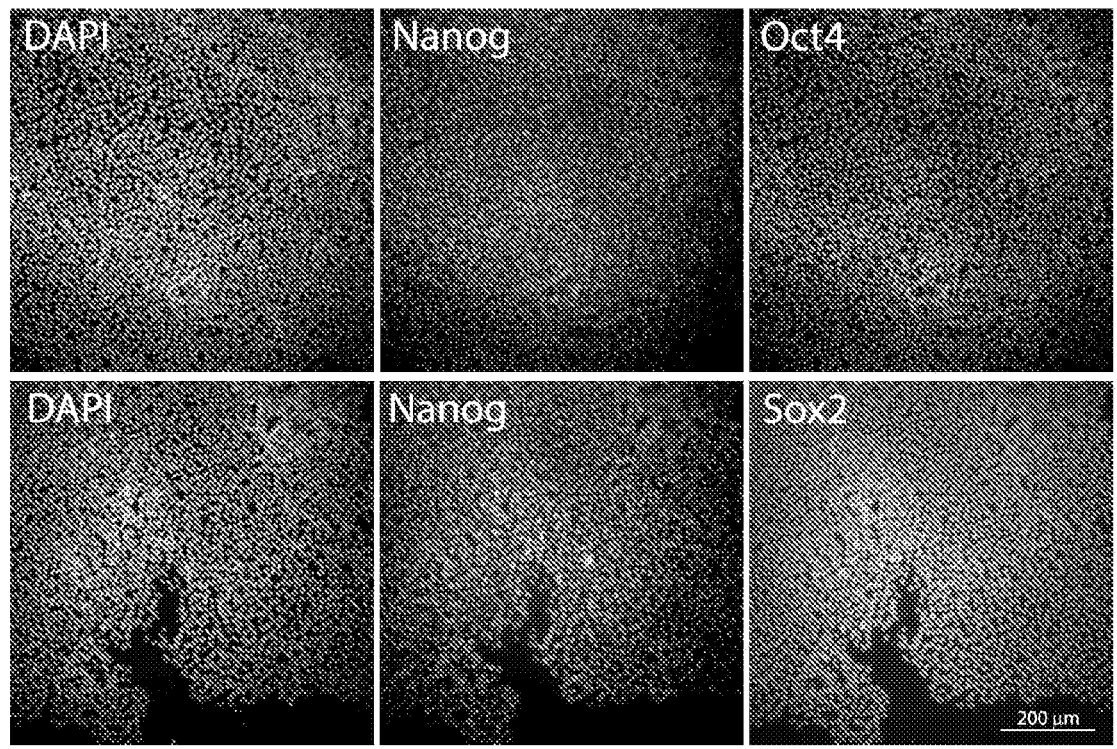
FIG. 2 shows representative photomicrographs of undifferentiated human embryonic stem cells (uhFSC) in accordance with the present disclosure stained by immunocytochemistry for pluripotency markers. The top row and bottom row of photomicrographs each show a single imaging field of uhFSCs that were stained for DAPI, Nanog, and Oct4 (top row) or DAPI, Nanog, and Sox2 (bottom row) and imaged on an IN Cell Analyzer 2000. Scale bar in the bottom right panel applies to all images in the figure.
Figure 3:
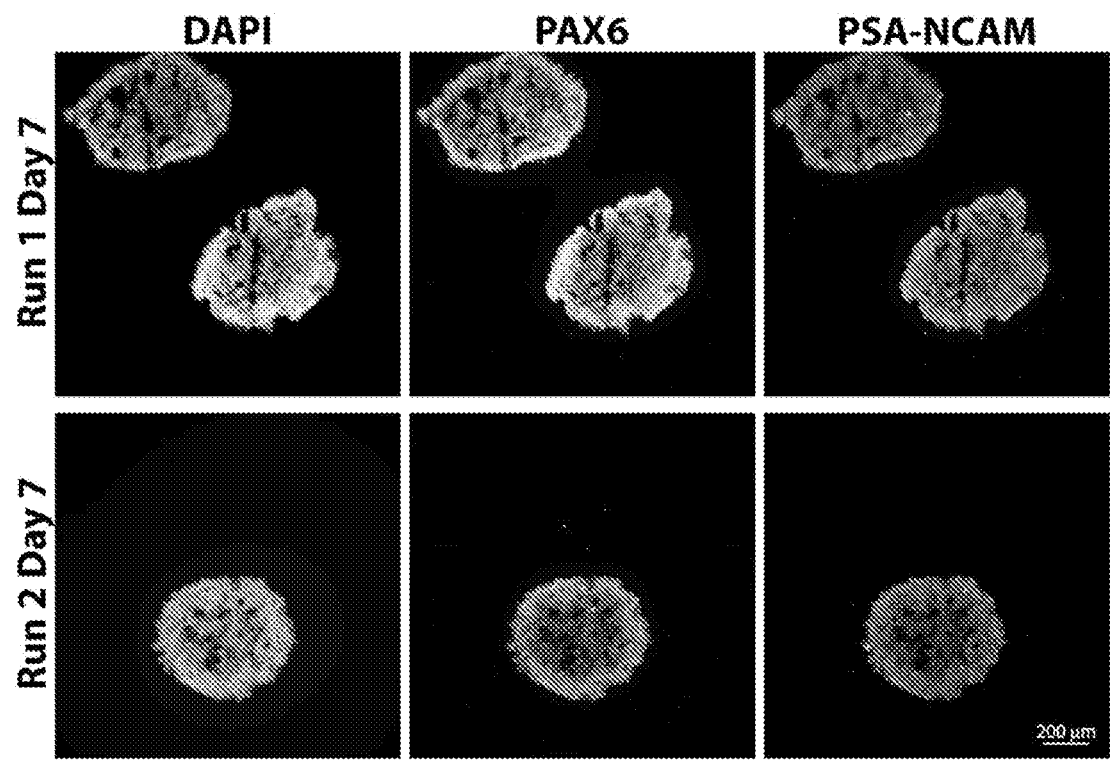
FIG. 3 shows representative photomicrographs of neuroectoderm progenitor cells generated as non-embryoid body (non-EB) aggregates in suspension in accordance with the present disclosure and stained by immunocytochemistry. The top row and bottom row of photomicrographs show aggregates of neuroectoderm progenitor cells generated from two representative experiments and stained by immunocytochemistry for DAPI (left panels), PAX6 (middle panels), and PSA-NCAM (right panels). Stained cellular aggregates were imaged on an IN Cell Analyzer 2000. Scale bar in the bottom right panel applies to all images in the figure.

FIG. 2 and FIG. 3 show representative ICC data for the starting pluripotent cell population and Day 7 neuroectoderm progenitor cells, respectively. As shown in FIG. 2, the starting population of undifferentiated human embryonic stem cells expressed the canonical pluripotency markers, Nanog, Oct4, and Sox2 (Wang Z, Oron E, Nelson B, Razis S, Ivanova N. Distinct lineage specification roles for NANOG, OCT4, and SOX2 in human embryonic stem cells. *Cell Stem Cell*. 2012 Apr. 6; 10 (4):440-54). After 7 days of differentiation, the cellular aggregates from two representative experiments expressed PAX6 and PSA-NCAM, two protein markers characteristic of neuroectoderm progenitor cells (FIG. 3, Lippmann E S, Williams C E, Ruhl D A, Estevez-Silva M C, Chapman E R, Coon J J, Ashton R S. Deterministic HOX patterning in human pluripotent stem cell-derived neuroectoderm. *Stem Cell Reports*. 2015 Apr. 14; 4 (4):632-44; Kim D S, Lee D R, Kim H S, Yoo J E, Jung S J, Lim B Y, Jang J, Kang H C, You S, Hwang D Y, Leem J W, Nam T S, Cho S R, Kim D W. Highly pure and expandable PSA-NCAM-positive neural precursors from human ESC and iPSC-derived neural rosettes. *PLoS One*. 2012; 7 (7):e39715).

For human embryonic stem cells differentiated through Day 42 into oligodendrocyte progenitor cells, protein marker expression in the resulting single cell population was characterized by both flow cytometry and ICC.

To characterize protein marker expression of the oligodendrocyte progenitor cells by ICC, staining was carried out as described above for slide-mounted aggregate sections, except permeabilization was performed with 100% methanol for 2 minutes at RT, and blocking solution consisted of 10% fetal bovine serum in PBS.

Figure 4:
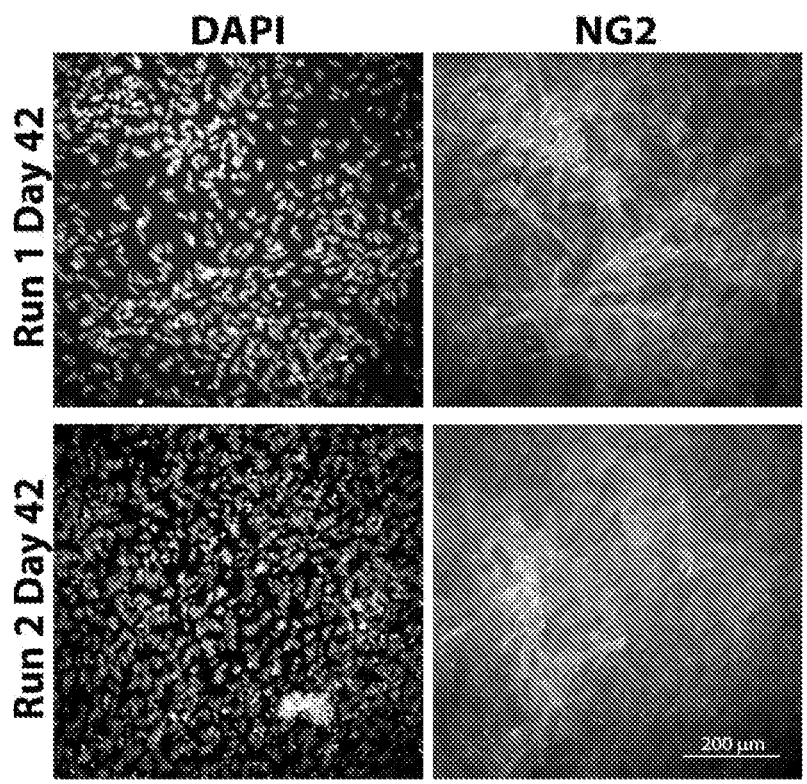
FIG. 4 shows representative photomicrographs of oligodendrocyte progenitor cells generated in accordance with the present disclosure and stained by immunocytochemistry. The top row and bottom row of photomicrographs show oligodendrocyte progenitor cells generated from two representative experiments and stained by immunocytochemistry for DAPI (left panels), and NG2 (right panels). Stained cells were imaged on an IN Cell Analyzer 2000. Scale bar in the bottom right panel applies to all images in the figure.

FIG. 4 shows representative ICC data for the Day 42 oligodendrocyte progenitor cells. The resulting single cell population from two representative experiments expressed the oligodendrocyte progenitor cell marker NG2 (Zhang Y, Chen K, Sloan S A, Bennett M L, Scholze A R, O'Keeffe S, Phatnani H P, Guarnieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci*. 2014 Sep. 3; 34 (36):11929-47).

To quantify cell surface markers on Day 42 by flow cytometry, cells were thawed in Thaw Medium (10% fetal bovine serum in DMEM medium), centrifuged and resuspended in Stain Buffer (2% fetal bovine serum/0.05% sodium azide in PBS). Cells were incubated with primary antibodies specific to markers of interest, including NG2 (Invitrogen #37-2300), GD3 (Millipore #MAB2053), A2B5 (BD #563775), CD49f (Millipore #CBL458P), EpCAM (Dako #M080401-2) and CLDN6 (Thermo Fisher #MA5-24076), and their isotype controls for 30 minutes on ice. Cells were washed with Stain Buffer to remove unbound antibodies; in the case of unconjugated antibodies, cells were then incubated with appropriate fluorophore-conjugated secondary antibodies for 30 minutes on ice. Cells were washed and propidium iodide was then added to demark dead cells. In some cases, cells were cultured overnight at 37° C./5% CO2 in tissue culture vessels coated with Matrigel (Corning #356231) to recover protein markers that exhibited sensitivity to the Day 42 harvesting procedure described in Example 4, and were then harvested with TrypLE™ Select (Thermo Fisher #A12859-01) and stained for flow cytometry analysis as described above. All cells were analyzed on an Attune NxT (Thermo Fisher, Waltham, MA, USA) flow cytometer. To calculate the percentage of cells expressing a given protein marker, dead cells staining with propidium iodine were gated and the number of viable cells bound to the corresponding antibody was expressed as a fraction of the total number of cells analyzed after correcting for the number of cells that exhibited non-specific binding to the isotype control antibody.

TABLE 1 shows representative flow cytometry data for Day 42 oligodendrocyte progenitor cells generated in accordance with the methodology described in Example 4. As shown for two representative runs, a high proportion of cells in the resulting cell population expressed characteristic oligodendrocyte markers, including NG2 (Zhang Y, Chen K, Sloan S A, Bennett M L, Scholze A R, O'Keeffe S, Phatnani H P, Guarnieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci.* 2014 Sep. 3; 34 (36):11929-47), and GD3 (Gallo V, Zhou J M, McBain C J, Wright P, Knutson P L, Armstrong R C. Oligodendrocyte progenitor cell proliferation and lineage progression are regulated by glutamate receptor-mediated K+ channel block. *J Neurosci.* 1996 Apr. 15; 16 (8):2659-70), as well as the pre-OPC marker, A2B5 (Keirstead H S, Nistor G, Bernal G, Totoiu M, Cloutier F, Sharp K, Steward O. Human embryonic stem cell-derived oligodendrocyte progenitor cell transplants remyelinate and restore locomotion after spinal cord injury. *J Neurosci.* 2005 May 11; 25 (19):4694-705). In addition, non-OPC markers were minimally detected in the resulting population, including the neural progenitor/epithelial marker CD49f (Krebsbach P H, Villa-Diaz L G. The Role of Integrin a6 (CD49f) in Stem Cells: More than a Conserved Biomarker. *Stem Cells Dev.* 2017 Aug. 1; 26 (15):1090-1099) and the epithelial markers CLDN6 (Lin D, Guo Y, Li Y, Ruan Y, Zhang M, Jin X, Yang M, Lu Y, Song P, Zhao S, Dong B, Xie Y, Dang Q, Quan C. Bioinformatic analysis reveals potential properties of human Claudin-6 regulation and functions. *Oncol Rep.* 2017 August; 38 (2):875-885) and EpCAM (Huang L, Yang Y, Yang F, Liu S, Zhu Z, Lei Z, Guo J. Functions of EpCAM in physiological processes and diseases (Review). *Int J Mol Med.* 2018 October; 42 (4):1771-1785).

TABLE 1

Representative flow cytometry data for oligodendrocyte progenitor cells produced by a method in accordance with the present disclosure.

| | OPC/Pre-OPC markers | | | Non-OPC markers | | |
|---|---|---|---|---|---|---|
| | NG2 | GD3 | A2B5 | CD49f | CLDN6 | EpCAM |
| Run 1 | 98% | 74% | 22% | 2% | 2% | 1% |
| Run 2 | 89% | 72% | 49% | 4% | 2% | 0% |

The cell population generated by the methodology described in the present disclosure resulted in higher proportion of cells positive for oligodendrocyte progenitor cell marker NG2 and reduced expression of non-OPC markers CD49f, CLDN6, and EpCAM when compared to OPCs that are currently in clinical testing to treat spinal cord injury and that were generated using another method (Priest C A, Manley N C, Denham J, Wirth E D 3rd, Lebkowski J S. Preclinical safety of human embryonic stem cell-derived oligodendrocyte progenitors supporting clinical trials in spinal cord injury. *Regen Med.* 2015 November; 10 (8):939-58; Manley N C, Priest C A, Denham J, Wirth E D 3rd, Lebkowski J S. Human Embryonic Stem Cell-Derived Oligodendrocyte Progenitor Cells: Preclinical Efficacy and Safety in Cervical Spinal Cord Injury. *Stem Cells Transl Med.* 2017 October; 6 (10):1917-1929).

Example 6—Characterization of Differentiated Cell Populations by Gene Expression Profiling Gene expression profiling can be used to characterize the cellular phenotype of the starting pluripotent cell population and each stage of differentiation, including the generation of neuroectoderm progenitor cells, glial progenitor cells, and oligodendrocyte progenitor cells. Gene expression profiling includes both global transcriptome profiling, using such methods as microarray and RNA-seq, and targeted gene profiling using methods of increased sensitivity such as quantitative real-time PCR (qPCR).

To perform gene expression profiling, cells were lysed in Qiagen RLT Lysis Buffer (Qiagen #79216), and RNA was purified using Qiagen RNeasy Mini Kit (Qiagen #74106) according to the manufacturer's guidelines. For qPCR-based analysis, purified RNA was then converted to cDNA according to standard methods using the Invitrogen Superscript IV VILO Mastermix (Thermo Fisher Scientific #11756050) according to the manufacturer's guidelines. The relative expression level of target genes and reference housekeeping genes was then quantified using gene-specific primer-probe sets (Applied Biosystems Taqman Gene Expression Assays, Thermo Fisher Scientific #4331182) according to the manufacturer's guidelines. To determine relative expression levels of a given set of target genes, PCR reactions were performed on the ABI 7900HT Real-Time Sequence Detection System (Applied Biosystems), the BioMark HD System (Fluidigm) or equivalent. Each target gene was normalized to one or multiple reference genes, such as GAPDH, to determine its relative expression level.

FIG. 5 shows a representative qPCR analysis of uhFSCs at the time of harvest prior to formation of three-dimensional cellular aggregates (Day −1) and 24 hours later, after formation of small, non-embryoid body (non-EB) aggregates (Day 0, immediately prior to initiation of neuroectoderm differentiation). Two representative experiments were conducted, and RNA samples were collected and processed for gene expression profiling by qPCR using the methods described above. Fluidigm qPCR was conducted using a 76 gene panel that consisted of known markers for pluripotency and early differentiation. For each gene, a normalized ACT value was calculated relative to the average of five housekeeping genes (ACTB, GAPDH, EP300, PGK1, SMAD1). The resulting correlation plots of all ACT values for Day −1 versus Day 0 are shown in FIG. 5, and indicate that the cells in Day 0 small non-EB aggregates retained expression of pluripotency genes and had a similar overall expression profile of the tested markers as the Day −1 uhFSC. This is further supported by the calculations of fold change relative to baseline presented in TABLE 2, which show high levels of the pluripotency markers, NANOG, LIN28A, and SOX2 at 24 hours after aggregate formation of uhFSCs (Day 0 uhFSCs) for both representative experiments.

TABLE 2 shows qPCR results from two representative experiments measuring expression of pluripotency genes, neuroectoderm progenitor genes, glial progenitor genes, and oligodendrocyte progenitor genes in cell populations generated by methods in accordance with the present disclosure. RNA samples were collected at the following time points: 24 hours after initiation of uhFSC cellular aggregate formation and prior to differentiation (Day 0), following differentiation to neuroectoderm progenitors (Day 7), following differentiation to glial progenitors (Day 21), and following differentiation to oligodendrocyte progenitors (Day 42). RNA samples were processed for qPCR using the methods described above. A selected panel of genes indicative of each differentiation state were quantified, including: three pluripotency genes (NANOG, LIN28A, SOX2), three neuroectoderm progenitor genes (PAX6, HES5, ZBTB16), three glial progenitor genes (CACGN4, FABP7, SOX6), and three oligodendrocyte progenitor genes (CSPG4, PDGFRα, DCN). For each gene, normalized ACT values were calculated using the average of five housekeeping genes (ACTB, GAPDH, EP300, PGK1, SMAD1), and fold expression relative to baseline (expression below the limit of quantification) was calculated using the ΔΔCT method.

Referring to TABLE 2, differentiation of uhFSCs for seven days by a method in accordance with the present disclosure resulted in a gene expression profile that was consistent with neuroectoderm progenitor cells, including downregulation of NANOG, and expression of LIN28A, SOX2, PAX6, HES5, and ZBTB16 (Patterson M, Chan D N, Ha I, Case D, Cui Y, Van Handel B, Mikkola H K, Lowly W E. Defining the nature of human pluripotent stem cell progeny. Cell Res. 2012 January; 22 (1):178-93; Lippmann E S, Williams C E, Ruhl D A, Estevez-Silva M C, Chapman E R, Coon J J, Ashton R S. Deterministic HOX patterning in human pluripotent stem cell-derived neuroectoderm. *Stem Cell Reports*. 2015 Apr. 14; 4 (4):632-44; Woo S M, Kim J, Han H W, Chae J I, Son M Y, Cho S, Chung H M, Han Y M, Kang Y K. Notch signaling is required for maintaining stem-cell features of neuroprogenitor cells derived from human embryonic stem cells. *BMC Neurosci*. 2009 Aug. 17; 10:97; Avantaggiato V, Pandolfi P P, Ruthardt M, Hawe N, Acampora D, Pelicci P G, Simeone A. Developmental analysis of murine Promyelocyte Leukemia Zinc Finger (PLZF) gene expression: implications for the neuromeric model of the forebrain organization. *J Neurosci*. 1995 July; 15 (7 Pt 1):4927-42).

After 21 days of suspension-based differentiation, the resulting cell population exhibited a gene expression profile that was consistent with glial progenitor cells, including downregulation of pluripotency and neuroectoderm progenitor cell markers and induction of CACNG4, FABP7, and SOX6 (Zhang Y, Chen K, Sloan S A, Bennett M L, Scholze A R, O'Keeffe S, Phatnani H P, Guamieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci*. 2014 Sep.

TABLE 2 qPCR analysis of gene markers for pluripotency, neuroectoderm progenitor cells (NEPCs), glial progenitor cells (GPCs), and oligodendrocyte progenitor cells (OPCs) in H1 uhESCs differentiated into OPCs in accordance with the present disclosure.

| | Run 1 Day 0 uhESC | Run 2 Day 0 uhESC | Run 1 Day 7 NEPC | Run 2 Day 7 NEPC | Run 1 Day 21 GPC | Run 2 Day 21 GPC | Run 1 Day 42 OPC | Run 2 Day 42 OPC |
|---|---|---|---|---|---|---|---|---|
| Pluripotency genes | | | | | | | | |
| NANOG | 236 | 244 | 2 | 2 | 2 | 1 | 2 | 1 |
| LIN28A | 410 | 203 | 240 | 160 | 3 | 1 | 2 | 1 |
| SOX2 | 603 | 628 | 1381 | 1337 | 661 | 453 | 12 | 18 |
| Neuroectoderm progenitor cell (NEPC) genes | | | | | | | | |
| PAX6 | 1 | 2 | 971 | 1329 | 180 | 193 | 2 | 2 |
| HES5 | 1 | 2 | 295 | 555 | 384 | 511 | 2 | 1 |
| ZBTB16 | 1 | 2 | 154 | 166 | 70 | 47 | 5 | 1 |
| Glial progenitor cell (GPC) genes | | | | | | | | |
| CACNG4 | 21 | 20 | 96 | 169 | 377 | 474 | 86 | 73 |
| FABP7 | 6 | 7 | 7 | 6 | 407 | 221 | 14 | 13 |
| SOX6 | 1 | 2 | 6 | 6 | 36 | 58 | 6 | 8 |
| Oligodendrocyte progenitor cell (OPC) genes | | | | | | | | |
| CSPG4 | 5 | 2 | 2 | 2 | 2 | 1 | 234 | 225 |
| PDGFRα | 1 | 2 | 4 | 2 | 4 | 2 | 32 | 88 |
| DCN | 1 | 2 | 2 | 2 | 30 | 17 | 753 | 803 |

3; 34 (36):11929-47; Petit A, Sanders A D, Kennedy T E, Tetzlaff W, Glattfelder K J, Dalley R A, Puchalski R B, Jones A R, Roskams A J. Adult spinal cord radial glia display a unique progenitor phenotype. *PLoS One.* 2011; 6 (9): e24538; Baroti T, Zimmermann Y, Schillinger A, Liu L, Lommes P, Wegner M, Stolt C C. Transcription factors Sox5 and Sox6 exert direct and indirect influences on oligodendroglial migration in spinal cord and forebrain. *Glia.* 2016 January; 64 (1):122-38).

Following 42 days of differentiation in accordance with the methods described in the present disclosure, the resulting cell population expressed markers consistent with oligodendrocyte progenitors, including downregulation of the earlier lineage markers and induction of CSPG4 (NG2), PDGFRα, and DCN (Zhang Y, Chen K, Sloan S A, Bennett M L, Scholze A R, O'Keeffe S, Phatnani H P, Guamieri P, Caneda C, Ruderisch N, Deng S, Liddelow S A, Zhang C, Daneman R, Maniatis T, Barres B A, Wu J Q. An RNA-sequencing transcriptome and splicing database of glia, neurons, and vascular cells of the cerebral cortex. *J Neurosci.* 2014 Sep. 3; 34 (36):11929-47).

Example 7—Differentiation of Human Embryonic Stem Cells to Neuroectoderm Progenitor Cells using Alternative Small Molecule Inhibitors of TGFBRVActivin/Nodal Signaling and BMP Signaling In addition to the small molecule inhibitors used in Example 2 (SB431542 and Dorsomorphin), alternative small molecule inhibitors of TGFβR1/Activin/Nodal signaling and BMP signaling were tested for their ability to differentiate human embryonic stem cells into neuroectoderm progenitors in suspension. TABLE 3 lists the alternative small molecule inhibitors that were tested. Each condition was tested in duplicate wells of an Ultra Low Attachment 6-well tissue culture plate (Corning #3471).

On differentiation Day 7, cells were collected and processed for RNA extraction and gene expression profiling by qPCR as described in Example 6. For each gene, a normalized ACT value was calculated relative to the average of five housekeeping genes (ACTB, GAPDH, EP300, PGK1, SMAD1), and fold expression relative to baseline (expression below the limit of quantification) was calculated using the AACT method. TABLE 4 shows the average of fold expression value for biological duplicates of each small molecule combination (relative to baseline). Referring to TABLE 4, differentiation of uhFSCs for seven days in suspension with each of the tested small molecule combinations resulted in downregulation of the pluripotency marker NANOG and a similar degree of maintained expression or induction of genes associated with a neuroectoderm progenitor cell phenotype, including LIN28A, SOX2, PAX6, HESS, and ZBTB16.

Figure 6A:
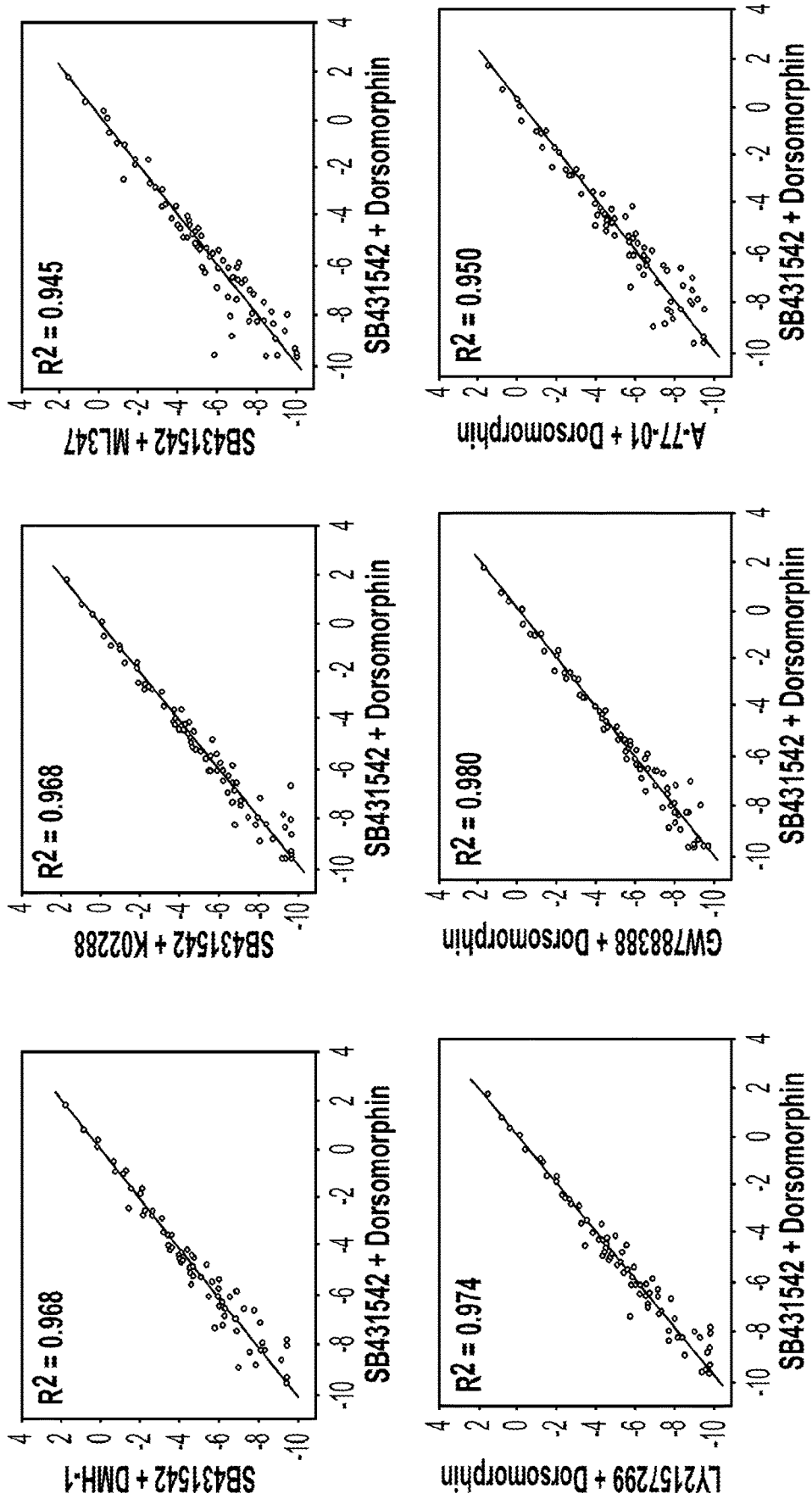
FIG. 6 shows correlation plots of the Day 7 gene expression profile of uhFSCs differentiated into neuroectoderm progenitor cells in suspension using different small molecule combinations. Each correlation plot shows a comparison of the Day 7 gene expression profile for cells treated with SB431542 plus Dorsomorphin versus the alternative small molecule combination indicated on the y-axis of each plot. For each plot, the data points represent each of the 96 genes assessed by Fluidigm qPCR and calculated as the normalized ΔCT as described in Example 7. R-squared values are shown in the upper left corner of each plot and were calculated based on the best-fit line using JMP software (SAS, Cary, NC, USA).
Figure 6B:
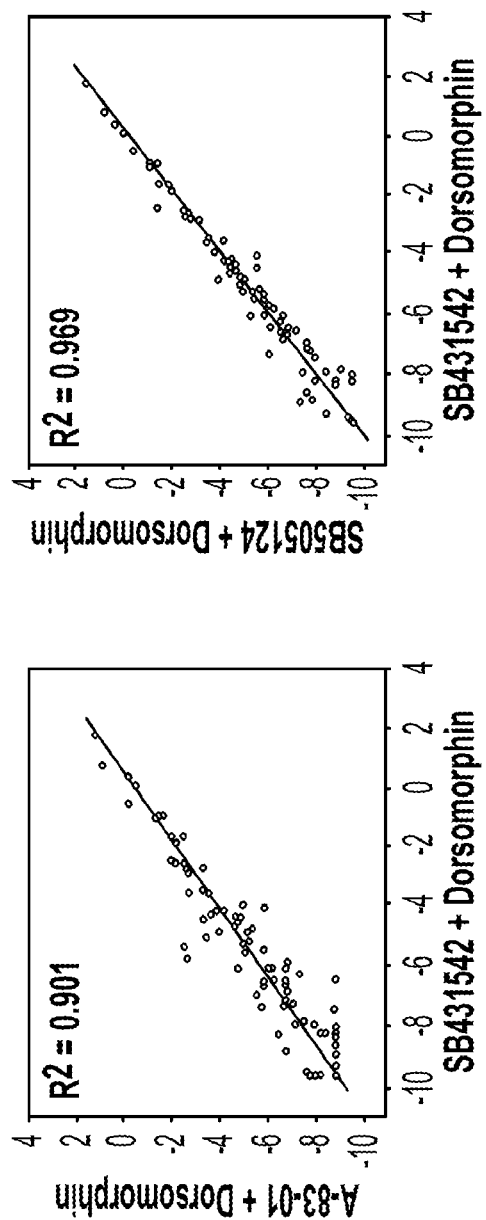

To obtain a more comprehensive comparison of the resulting Day 7 cellular phenotypes after treatment with each small molecule combination, Fluidigm qPCR was conducted using a 96 gene panel that consisted of known markers for pluripotency, neuroectoderm progenitor cells, neural tube patterning, glial progenitor cells, oligodendrocyte progenitor cells, neural crest cells, neurons, astrocytes, pericytes, Schwann cells, and epithelial cells. Referring to FIG. 6, comparison of the day 7 cellular phenotype for each alternative small molecule combination to the cellular phenotype generated by treatment with SB431542 plus Dorsomorphin by regression plot of the normalized ACT values indicated that a similar overall cellular phenotype could be achieved with each of the small molecule combinations tested. Taken together, the results shown in TABLE 4 and FIG. 6 support that various combinations of: (i) a TGFβR1/Activin/Nodal signaling inhibitor, together with (ii) a BMP signaling inhibitor, can be used to differentiate uhFSCs to neuroectoderm progenitor cells in suspension, and further to glial progenitor cells and to oligodendrocyte progenitor cells using the methods of the present disclosure.

TABLE 3

Small molecule inhibitors used to differentiate human embryonic stem cells into neuroectoderm progenitors in suspension.

| Inhibitor | Concentration tested | Primary binding target(s) | Vendor catalogue # |
|---|---|---|---|
| TGFDR1/Activin/Nodal inhibitors | | | |
| SB431542 | 10 μM | ALK5, ALK4, ALK7 | Sigma-Aldrich # S4317 |
| LY2 157299 | 10 μM | ALK5 | ApexBio # A8348 |
| GW788388 | 10 μM | ALK5, ALK4, ALK7 | ApexBio # A8301 |
| A-77-01 | 10 μM | ALK5 | ApexBio # A3132 |
| A-83-01 | 10 μM | ALK5, ALK4, ALK7 | ApexBio # A3133 |
| SB505124 | 10 μM | ALK5, ALK4, ALK7 | ApexBio # A3799 |
| BMP inhibitors | | | |
| Dorsomorphin | 2 μM | ALK2, ALK3, ALK6 | Sigma-Aldrich # P5499 |
| DMH-1 | 2 μM | ALK2, ALK3 | ApexBio # B3686 |
| K02288 | 2 μM | ALK2, ALK1, ALK3, ALK6 | ApexBio # B2286 |
| ML347 | 2 μM | ALK2, ALK1 | ApexBio # B3688 |

TABLE 4 qPCR analysis of gene markers for pluripotency and neuroectoderm progenitor cells (NEPCs) in Ill uhESCs differentiated into NEPCs using different combinations of small molecule inhibitors.

| | SB431542 + Dorso | SB431542 + DMH-1 | SB431542 + K02288 | SB431542 + 1V1L347 | LY2157299 + Dorso | GW788388 + Dorso | A-77-01 + Dorso | A-83-01 + Dorso | SB505124 + Dorso |
|---|---|---|---|---|---|---|---|---|---|
| Pluripotency genes | | | | | | | | | |
| NANOG | 2 | 4 | 1 | 1 | 3 | 2 | 3 | 2 | 2 |
| LIN28A | 518 | 473 | 684 | 565 | 554 | 607 | 648 | 646 | 596 |
| SOX2 | 1335 | 1488 | 1412 | 1257 | 1325 | 1270 | 1385 | 1395 | 1349 |
| Neuroectoderm progenitor cell genes | | | | | | | | | |
| PAX6 | 791 | 836 | 741 | 615 | 748 | 692 | 791 | 514 | 765 |
| HESS | 1025 | 862 | 1047 | 698 | 1040 | 1012 | 876 | 650 | 980 |
| ZBTB16 | 201 | 192 | 210 | 220 | 203 | 198 | 198 | 159 | 188 |

Example 8—Assessing the Presence of Extraneous Epithelial Lineage Cells in the Differentiated OPC Population using an In Vitro Cyst Assay Presence of undesirable epithelial lineage cells in an OPC population generated in accordance with the present disclosure was tested using an in vitro cyst assay. The cyst assay was performed essentially according to a protocol by Debnath et al. (Debnath J, Muthuswamy S K, Brugge J S. Morphogenesis and oncogenesis of MCF-10A mammary epithelial acini grown in three-dimensional basement membrane cultures. 2003 *Methods*. 3:256-68). Briefly, OPCs were grown in a 3D culture system in the presence of factors known to stimulate epithelial cyst formation for a period of 20 days. In addition to visual detection of cysts, the presence of cystic structures containing basolateral protein expression of the epithelial marker CD49f was also assessed using immunocytochemistry.

OPCs were seeded in cyst-supporting media onto a pad of Matrigel® (Corning) at a density of $21.9\times10^3$ cells/cm$^2$ (in total, $0.5\times10^6$ cells were seeded in 12 wells of a 24 well plate). Cells were cultured for 20 days. On Day 20, a live cyst count was performed, Matrigel® was dissolved using Cell Recovery Solution (Corning #354253), cells were fixed in 4% paraformaldehyde (PFA) for 5 minutes on ice and permeabilized in blocking buffer overnight. Subsequently, cysts were stained for CD49f (ITGA6), phalloidin, and counter-stained with DAPI. Cysts were imaged using IN Cell Analyzer 2000 (GE Healthcare Life Sciences) and cyst frequency, size and staining intensity were quantified using IN Cell Developer Software (GE Healthcare Life Sciences) and MATLAB™ (Mathworks).

Referring to TABLE 5, OPCs generated from two representative runs using a method in accordance with the present disclosure and tested in the in vitro cyst assay produced fewer cysts than that of three control lots of OPCs (Control A, Control B and Control C) that were generated by an alternative method previously found to give rise to epithelial cyst formation in vivo (Manley N C, Priest C A, Denham J, Wirth E D 3rd, Lebkowski J S. Human Embryonic Stem Cell-Derived Oligodendrocyte Progenitor Cells: Preclinical Efficacy and Safety in Cervical Spinal Cord Injury. *Stem Cells Transl Med*. 2017 October; 6 (10):1917-1929). Based on these results, it is expected that OPCs generated in accordance with the present disclosure would form little or no epithelial cysts in vivo.

TABLE 5

Representative cyst assay results for oligodendrocyte progenitor cells produced by a method in accordance with the present disclosure.

| | Control A | Control B | Control C | Run 1 | Run 2 |
|---|---|---|---|---|---|
| Cysts/100,000 cell input | 6.2 | 16.8 | 25.6 | 0.4 | 0.4 |

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all aspects falling within the scope and spirit of the appended claims.

What is claimed is:

1. A method for obtaining a population of cells comprising glial progenitor cells from undifferentiated human pluripotent stem cells, the method comprising:
    a) obtaining a suspension culture of non-embryoid body (non-EB) aggregates of undifferentiated human pluripotent stem cells, wherein the human pluripotent stem cells remain in an undifferentiated state;
    b) culturing the non-EB aggregates from a) in dynamic suspension in the presence of at least one inhibitor of transforming growth factor beta (TGFβ)/Activin/Nodal signaling selected from an inhibitor of activin receptor-like kinase 5 (ALK5), SB431542, LY2157299, GW788388, A-77-01, A-83-01 or SB505124 and at least one inhibitor of bone morphogenetic protein (BMP) signaling selected from an activin receptor-like kinase 2 (ALK2), Dorsomorphin, DMH-1, K02288, ML3467, LDN193189 or Noggin protein for a first time period, thereby inducing differentiation to neuroectoderm lineage cells, wherein the first time period is three to four days;
    c) culturing the neuroectoderm lineage cells from b) in dynamic suspension in the presence of retinoic acid and at least one agonist of Smoothened receptor for a second time period, wherein the second time period is three to four days; and d) culturing the neuroectoderm lineage cells from c) in dynamic suspension in the presence of basic fibroblast growth factor (bFGF) and epidermal growth factor (EGF) for a further time period, until the cells have matured into glial progenitor cells, wherein steps a) through d) are performed over a period of about 21 days, wherein about refers to a variation of ±10%.

2. The method of claim 1, further comprising an additional step of harvesting the glial progenitor cells from d) and plating them onto a substrate.

3. The method of claim 2, wherein the substrate is recombinant human laminin-521.

4. The method of claim 1, wherein the human pluripotent stem cells are human embryonic stem cells (hESCs) or human induced pluripotent stem cells (hiPSCs).

5. The method of claim 1, wherein the at least one Smoothened receptor agonist is selected from the group consisting of Purmorphamine, Smoothened Agonist and Sonic Hedgehog (SHH) protein.

6. A method for obtaining a population of cells comprising oligodendrocyte progenitor cells (OPCs) from undifferentiated human pluripotent stem cells, the method comprising:
   a) obtaining glial progenitor cells according to the method of claim 1;
   b) harvesting the cells from a) and plating them onto a substrate; and
   c) culturing the cells from b) in the presence of epidermal growth factor (EGF) and platelet-derived growth factor AA (PDGF-AA) for a further time period, until the cells have matured into OPCs, wherein the OPCs express one or more markers selected from neural/glial antigen 2 (NG2), platelet-derived growth factor receptor A (PDGFRα), and ganglioside GD3 (GD3).

7. The method of claim 6, wherein the culturing of step c performed for a period of about 21 days.

8. The method of claim 6, wherein the substrate is selected from: (i) a cell adhesion peptide and (ii) an extracellular matrix selected from laminin and vitronectin.

9. The method of claim 6, wherein the substrate is recombinant human laminin-521 or laminin-511 E8 fragment.

10. The method of claim 6, wherein the human pluripotent stem cells are hESCs or hiPSCs.

11. A method for inducing differentiation of human pluripotent stem cells into paired box 6 (PAX6) positive neuroectoderm cells, the method comprising:
   a) obtaining a suspension culture of non-embryoid body (non-EB) aggregates of undifferentiated human pluripotent stem cells, wherein the human pluripotent stem cells remain in an undifferentiated state;
   b) culturing the non-EB aggregates from a) in dynamic suspension in the presence of at least one inhibitor of transforming growth factor beta (TGFβ)/Activin/Nodal signaling selected from an inhibitor of activin receptor-like kinase 5 (ALK5), SB431542, LY2157299, GW788388, A-77-01, A-83-01 or SB505124 and at least one inhibitor of bone morphogenetic protein (BMP) signaling selected from an activin receptor-like kinase 2 (ALK2), Dorsomorphin, DMH-1, K02288, ML3467, LDN193189 or Noggin protein for a first time period, thereby inducing differentiation to neuroectoderm lineage cells, wherein the first time period is three to four days;
   c) culturing the neuroectoderm lineage cells from b) in dynamic suspension in the presence of retinoic acid and at least one agonist of Smoothened receptor for a second time period, wherein the second time period is three to four days; until the cells have matured into paired box 6 (PAX6) positive neuroectoderm cells.

12. The method of claim 11, wherein the human pluripotent stem cells are human embryonic stem cells (hESCs) or human induced pluripotent stem cells (hiPSCs).

13. The method of claim 11, wherein the at least one Smoothened receptor agonist is A selected from the group consisting of Purmorphamine, Smoothened Agonist and Sonic Hedgehog (SHH) protein.

14. The method of claim 11, wherein steps a) through c) are performed over a period of about 7 to 8 days, wherein about refers to a variation of 10%.

15. A method for obtaining a population of cells comprising glial progenitor cells from undifferentiated human pluripotent stem cells, the method comprising:
   a) culturing undifferentiated human pluripotent stem cells that have been disaggregated and form a single-cell suspension in dynamic suspension to obtain non-embryoid body (non-EB) aggregates, wherein the human pluripotent stem cells in the non-EB aggregates remain in an undifferentiated state;
   b) culturing the non-EB aggregates from a) in dynamic suspension in the presence of at least one inhibitor of transforming growth factor beta (TGFf3)/Activin/Nodal signaling selected from an inhibitor of activin receptor-like kinase 5 (ALK5), SB431542, LY2157299, GW788388, A-77-01, A-83-01 or SB505124 and at least one inhibitor of bone morphogenetic protein (BMP) signaling selected from an activin receptor-like kinase 2 (ALK2), Dorsomorphin, DMH-1, K02288, ML3467, LDN193189 or Noggin protein for a first time period, thereby inducing differentiation to neuroectoderm lineage cells, wherein the first time time period is three to four days;
   c) culturing the neuroectoderm lineage cells from b) in dynamic suspension in the presence of retinoic acid and at least one agonist of Smoothened receptor for a second time period, wherein the second time period is three to four days; and
   d) culturing the neuroectoderm lineage cells from c) in dynamic suspension in the presence of basic fibroblast growth factor (bFGF) and epidermal growth factor (EGF) for a further time period, until the cells have matured into glial progenitor cells, wherein steps a) through d) are performed over a period of 21 days.

* * * * *